(12) United States Patent
Huang et al.

(10) Patent No.: US 10,319,920 B2
(45) Date of Patent: Jun. 11, 2019

(54) CARBAZOLE DERIVATIVES AND ORGANIC LIGHT-EMITTING DIODES BY USING THE SAME

(71) Applicant: Yuan Ze University, Chung-Li (TW)

(72) Inventors: Jau-Jiun Huang, Chung-Li (TW);
Man-Kit Leung, Chung-Li (TW);
Tien-Lung Chiu, Chung-Li (TW);
Jiun-Haw Lee, Chung-Li (TW);
Lik-Ka Yun, Chung-Li (TW)

(73) Assignee: YUAN ZE UNIVERSITY, Chung-Li (TW)

( * ) Notice: Subject to any disclaimer, the term of this patent is extended or adjusted under 35 U.S.C. 154(b) by 321 days.

(21) Appl. No.: 15/413,979

(22) Filed: Jan. 24, 2017

(65) Prior Publication Data

US 2018/0151808 A1    May 31, 2018

(30) Foreign Application Priority Data

Nov. 30, 2016  (TW) .............................. 105139531 A

(51) Int. Cl.
*H01L 51/50*  (2006.01)
*H01L 51/00*  (2006.01)
(Continued)

(52) U.S. Cl.
CPC ........ *H01L 51/0072* (2013.01); *C07D 209/86* (2013.01); *C07D 401/14* (2013.01);
(Continued)

(58) Field of Classification Search
None
See application file for complete search history.

(56) References Cited

U.S. PATENT DOCUMENTS

2015/0243902 A1* 8/2015 Wang .................. H01L 51/0069
257/40
2018/0170914 A1* 6/2018 Miyata ................. C07D 401/14

FOREIGN PATENT DOCUMENTS

CN         105418486 A    3/2016
WO    WO 2016/086885 A1   6/2016

* cited by examiner

*Primary Examiner* — Gregory D Clark
(74) *Attorney, Agent, or Firm* — Muncy, Geissler, Olds & Lowe, P.C.

(57) ABSTRACT

A carbazole derivative is shown in General Formula (1), (Continued)

wherein $R_1$ is selected from the group consisting of the structures according to the following General Formula (2), General Formula (3) and General Formula (4),

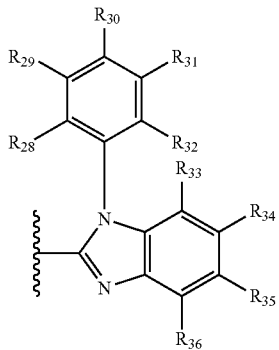

General Formula (2)

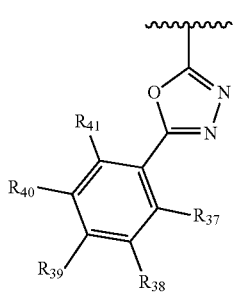

General Formula (3)

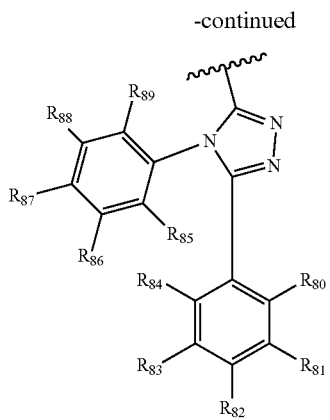

General Formula (4)

-continued wherein $R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

20 Claims, 1 Drawing Sheet

(51) Int. Cl.
  *C07D 209/86*   (2006.01)
  *C07D 401/14*   (2006.01)
  *C07D 413/14*   (2006.01)
  *C09K 11/02*   (2006.01)
  *C09K 11/06*   (2006.01)
(52) U.S. Cl.
  CPC .......... *C07D 413/14* (2013.01); *C09K 11/025* (2013.01); *C09K 11/06* (2013.01); *H01L 51/007* (2013.01); *H01L 51/0067* (2013.01); *C09K 2211/1007* (2013.01); *C09K 2211/1029* (2013.01); *C09K 2211/185* (2013.01); *H01L 51/0085* (2013.01); *H01L 51/5016* (2013.01); *H01L 2051/0063* (2013.01); *H01L 2251/552* (2013.01)

CARBAZOLE DERIVATIVES AND ORGANIC LIGHT-EMITTING DIODES BY USING THE SAME

CROSS REFERENCE TO RELATED APPLICATIONS

This Non-provisional application claims priority under 35 U.S.C. § 119(a) on Patent Application No(s). 105139531 filed in Taiwan, Republic of China on Nov. 30, 2016, the entire contents of which are hereby incorporated by reference.

BACKGROUND OF THE INVENTION

Field of Invention

The present invention relates to electroluminescent materials and light-emitting elements by using the same and, in particular, to carbazole derivatives and organic light-emitting diodes by using the same.

Related Art

With the advances in electronic technology, a light weight and high efficiency flat display device has been developed. An organic electroluminescent device possibly becomes the mainstream of the next generation flat panel display device due to its advantages of self-luminosity, no restriction on viewing angle, power conservation, simple manufacturing process, low cost, high response speed, full color and so on.

In general, the organic electroluminescent device includes an anode, an organic luminescent layer and a cathode. When applying a direct current to the organic electroluminescent device, electron holes and electrons are injected into the organic luminescent layer from the anode and the cathode, respectively. Charge carriers move and then recombine in the organic luminescent layer because of the potential difference caused by an applied electric field. The excitons generated by the recombination of the electrons and the electron holes may excite the luminescent molecules in the organic luminescent layer. The excited luminescent molecules then release the energy in the form of light.

Nowadays, the organic electroluminescent device usually adopts a host-guest emitter system. The organic luminescent layer disposed therein includes a host material and a guest material. The electron holes and the electrons are mainly transmitted to the host material to perform recombination and thereby generate energy, and then the energy is transferred to the guest material to generate light. The guest material can be categorized into fluorescent material and phosphorescent material. Theoretically, the internal quantum efficiency can approach 100% by using appropriate phosphorescent materials. Therefore, the phosphorescent materials recently have become one of the most important developments in the field of organic electroluminescent materials.

In the development of blue host materials, the triplet energy level of the host materials must be higher than or equal to that of the guest materials to avoid the energy lost caused by reverse energy transfer. The energy lost can result in low luminous efficiency (i.e., low current efficiency) and short lifespan, etc. Therefore, it is necessary for the host materials to have greater triplet energy level. In order to increase the triple energy level of the blue host materials, much research has been focused on the single benzene ring with various ortho-substituted groups. In ortho-substitution with electron-transporting group (e.g., Oxadiazole or 3-(Biphenyl-4-yl)-5-(4-tert-butylphenyl)-4-phenyl-4H-1,2,4-triazole) and hole-transporting group (e.g., Carbazoles), the 7c-conjugation of the molecular is interrupted due to steric hindrance and a bipolar molecule is created.

Besides, the selection of organic electroluminescent material is not only based on the matching energy level but also the high temperature of decomposition to avoid pyrolysis caused by high temperature and also avoid the resulted decreasing of stability.

Accordingly, the present invention is provided carbazole derivatives and organic light-emitting diodes by using the same which have high triplet energy level and fine thermal stability.

SUMMARY OF THE INVENTION

In view of the foregoing objectives, the invention provides a series of carbazole derivatives and organic light-emitting diodes by using the same. The carbazole derivatives have high triplet energy level and fine thermal stability.

A carbazole derivative according to the present invention has a structure of the following General Formula (1).

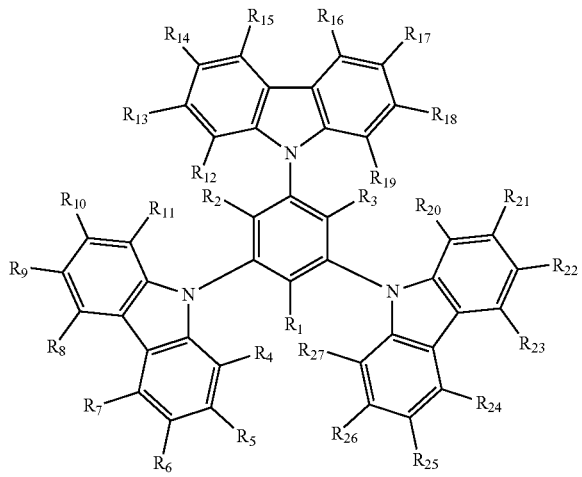

General Formula (1)

$R_1$ is selected from the group consisting of the structures according to the following General Formula (2), General Formula (3) and General Formula (4).

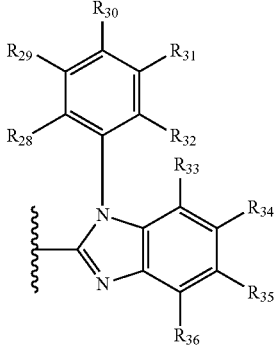

General Formula (2)

-continued

General Formula (3)

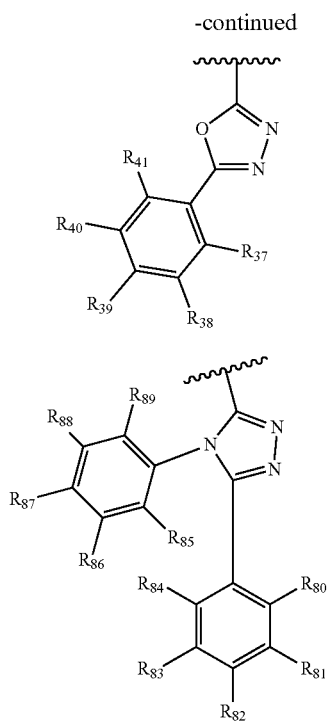

General Formula (4)

R₂ to R₄₁ and R₈₀ to R₈₉ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

A carbazole derivative according to the present invention has a structure of the following General Formula (5).

General Formula (5)

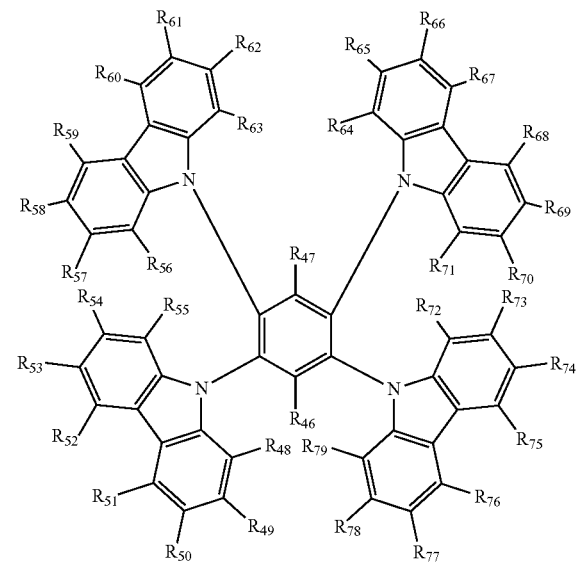

$R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group.

General Formula (2)

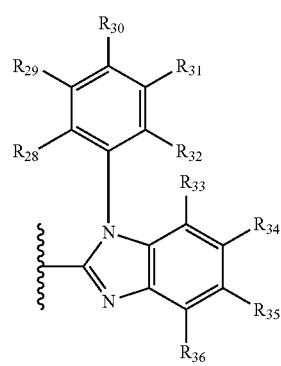

General Formula (3)

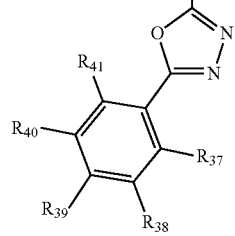

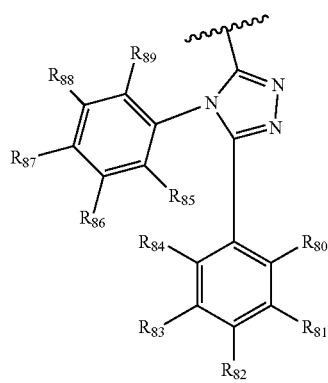

General Formula (4)

$R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

An organic light-emitting diode which is also provided includes a first electrode layer, a second electrode layer and an organic luminescent unit. The organic luminescent unit is disposed between the first electrode layer and the second electrode layer. The organic luminescent unit has at least a carbazole derivative as shown in General Formula (1).

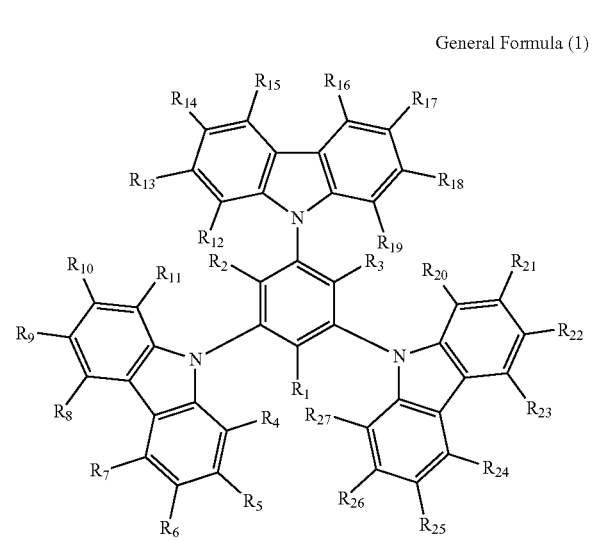

General Formula (1)

$R_1$ is selected from the group consisting of the structures according to the following General Formula (2), General Formula (3) and General Formula (4).

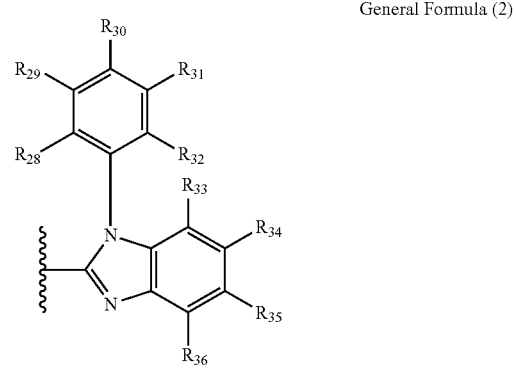

General Formula (2)

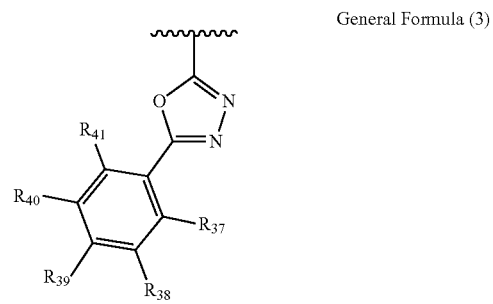

General Formula (3)

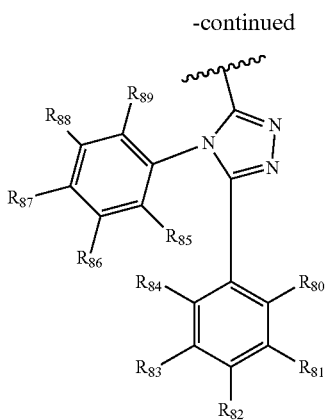

General Formula (4)

$R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

In one embodiment, the organic luminescent unit comprises an organic luminescent layer.

In one embodiment, the organic luminescent unit further comprises a hole transport layer and an electron transport layer, wherein the organic luminescent layer is disposed between the hole transport layer and the electron transport layer.

In one embodiment, the organic luminescent unit further comprises a hole transport layer, an electron blocking layer, an electron transport layer and an electron injection layer, wherein the electron blocking layer, the organic luminescent layer and the electron transport layer are sequentially disposed between the hole transport layer and the electron injection layer.

In one embodiment, the organic luminescent layer comprises a host material and a guest material, wherein the host material is the carbazole derivative and the guest material is a phosphorescent material.

In one embodiment, the content of the host material in the organic luminescent layer is between 60 vol % to 95 vol %.

In one embodiment, the content of the guest material in the organic luminescent layer is between 5 vol % to 40 vol %.

An organic light-emitting diode which is also provided includes a first electrode layer, a second electrode layer and an organic luminescent unit. The organic luminescent unit is disposed between the first electrode layer and the second electrode layer. The organic luminescent unit has at least a carbazole derivative as shown in General Formula (5).

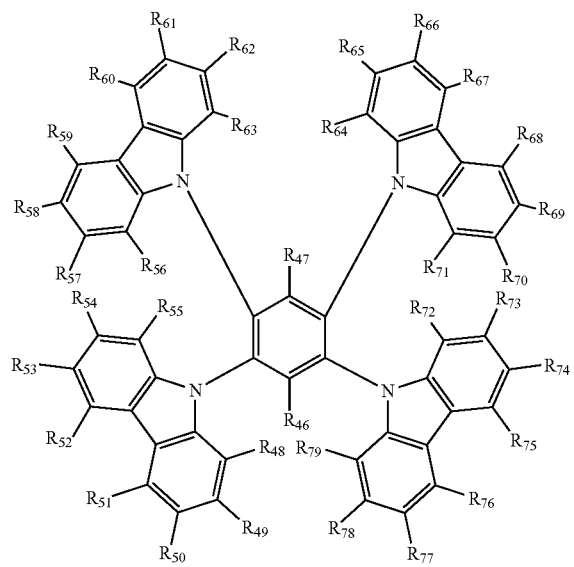

General Formula (5)

$R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group.

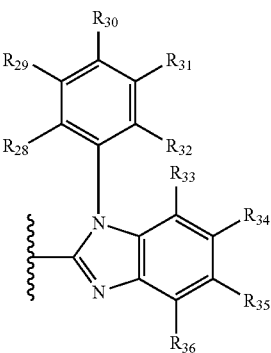

General Formula (2)

-continued

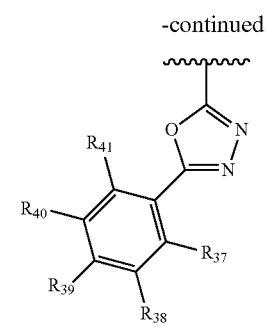

General Formula (3)

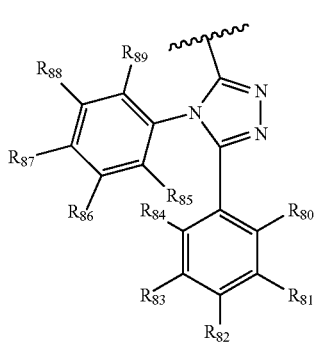

General Formula (4)

$R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 3 to 6. The cycloalkyl group is a substituted or unsubstituted cycloalkyl group with the carbon number of 3 to 6. The alkoxy group is selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6. The silyl group is selected from the group consisting of a substituted or unsubstituted straight-chain silyl group with the carbon number of 1 to 6, and a substituted or unsubstituted branched-chain silyl group with the carbon number of 3 to 6. The alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

In one embodiment, the organic luminescent unit comprises an organic luminescent layer.

In one embodiment, the organic luminescent unit further comprises a hole transport layer and an electron transport layer, wherein the organic luminescent layer is disposed between the hole transport layer and the electron transport layer.

In one embodiment, the organic luminescent unit further comprises a hole transport layer, an electron blocking layer, an electron transport layer and an electron injection layer, wherein the electron blocking layer, the organic luminescent layer and the electron transport layer are sequentially disposed between the hole transport layer and the electron injection layer.

In one embodiment, the organic luminescent layer comprises a host material and a guest material, wherein the host material is the carbazole derivative and the guest material is a phosphorescent material.

In one embodiment, the content of the host material in the organic luminescent layer is between 60 vol % to 95 vol %.

In one embodiment, the content of the guest material in the organic luminescent layer is between 5 vol % to 40 vol %.

As mentioned above, in the carbazole derivatives and the organic light-emitting diodes by using the same according to the present invention, it utilizes 1,3,5-Tris(carbazol-9-yl) benzene (TCP) or 1,2,4,5-tetra(9H-carbazol-9-yl)benzene (o-4Cbz) as a core structure and various kinds of electron-transporting groups as substituents at ortho-position to synthesize a series of bipolar host materials in phosphorescent organic light-emitting diodes with high luminous efficiency and good thermal stability. In addition, the carbazole derivatives of the present invention can also be applied to the hole transport layer. Moreover, 1,2,4,5-tetra(9H-carbazol-9-yl) benzene (o-4Cbz) can also be the host material and the hole transport layer material.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
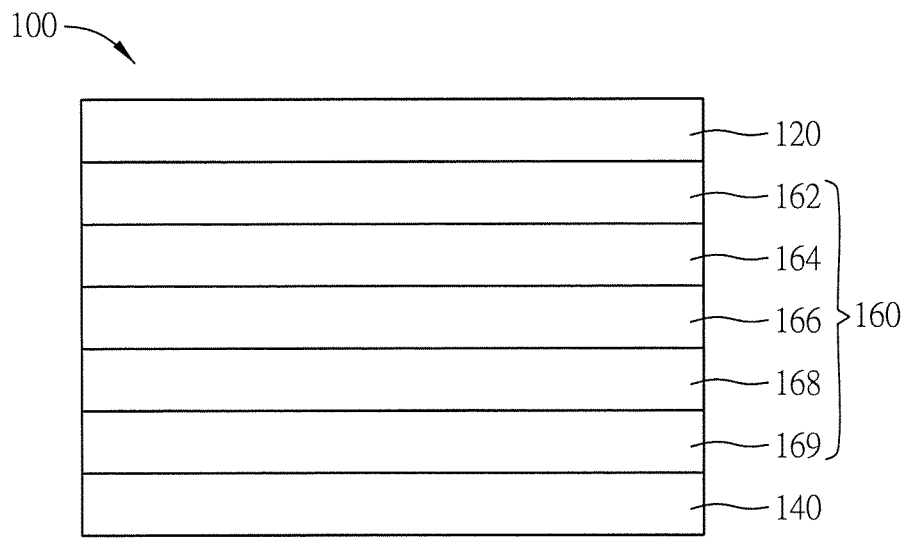
FIG. 1 is a cross-sectional schematic diagram of an organic light-emitting diode of the third embodiment according to the invention.

The embodiments of the invention will be apparent from the following detailed description, which proceeds with reference to the accompanying drawings, wherein the same references relate to the same elements.

Carbazole Derivatives

A carbazole derivative according to the first embodiment of the present invention has a structure of the following General Formula (1).

General Formula (1)

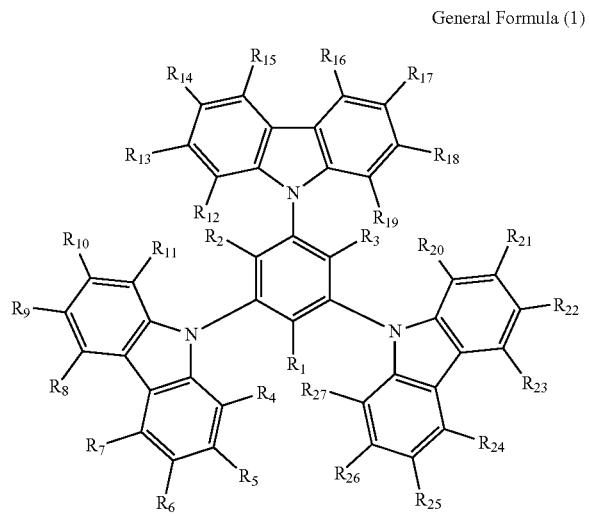

$R_1$ is selected from the group consisting of the structures according to the following General Formula (2), General Formula (3) and General Formula (4).

General Formula (2)

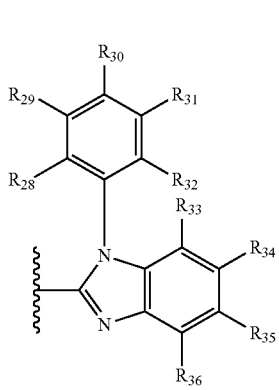

General Formula (3)

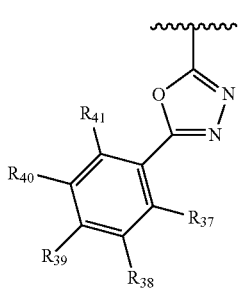

General Formula (4)

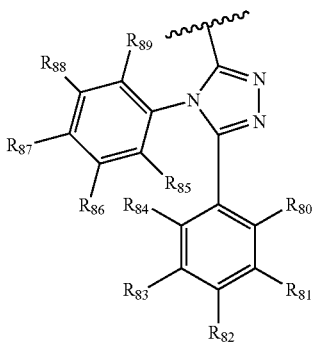

$R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

Herein, the alkyl group can be selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be a substituted or unsubstituted cycloalkyl group with the carbon number of 3 to 6. The alkoxy group can be selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be selected from the group consisting of a substituted or unsubstituted straight-chain haloalkyl group with the carbon number of 1 to 6, and a substituted or unsubstituted branched-chain haloalkyl group with the carbon number of 3 to 6, The thioalkyl group can be selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be selected from the group consisting of a substituted or unsubstituted straight-chain silyl group with the carbon number of 1 to 6, and a substituted or unsubstituted branched-chain silyl group with the carbon number of 3 to 6. The alkenyl group can be selected from the group consisting of a substituted or unsubstituted straight-chain alkenyl group with the carbon number of 2 to 6, and a substituted or unsubstituted branched-chain alkenyl group with the carbon number of 3 to 6.

The carbazole derivative of General Formula (1) according to the embodiment can be a host material of an organic luminescent layer in an organic light-emitting diode. A preferred example is the compound of Chemical Formula (1), o-3CbzBz, where $R_1$ is the structure of the following General Formula (2) and $R_2$ to $R_{36}$ are all independent hydrogen atoms.

General Formula (2)

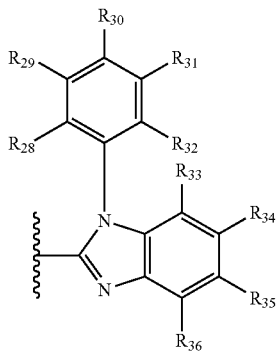

Chemical Formula (1)

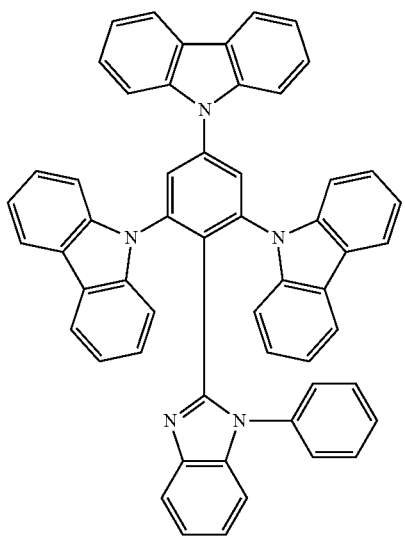

Alternatively, another preferred example is the compound of Chemical Formula (2), o-3CbzOXD, where $R_1$ is the structure of the following General Formula (3), and $R_2$ to $R_{27}$ and $R_{37}$ to $R_{41}$ are all independent hydrogen atoms, General Formula (3)

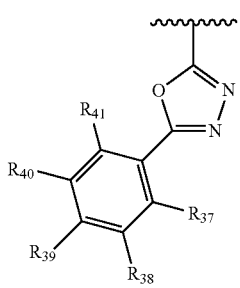

Chemical Formula (2)

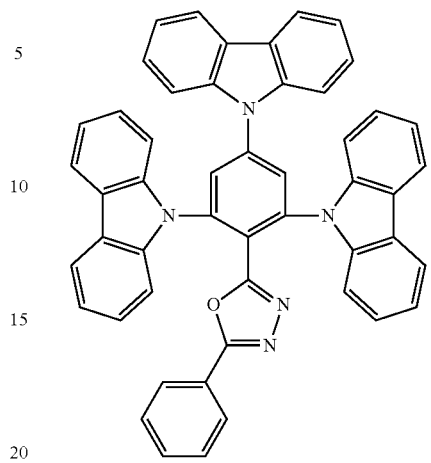

Alternatively, another preferred example is the compound of Chemical Formula (3), o-3CbzTAZ, where $R_1$ is the structure of the following General Formula (4), and $R_2$ to $R_{27}$ and $R_{80}$ to $R_{89}$ are all independent hydrogen atoms.

General Formula (4)

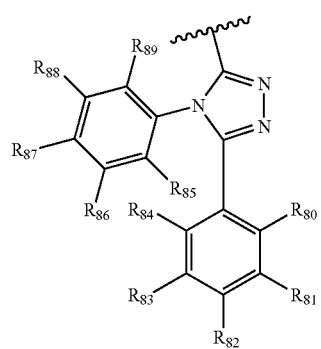

Chemical Formula (3)

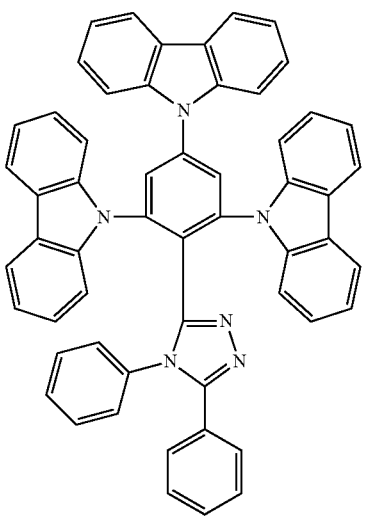

A carbazole derivative according to the second embodiment of the present invention has a structure of the following General Formula (5).

General Formula (5)

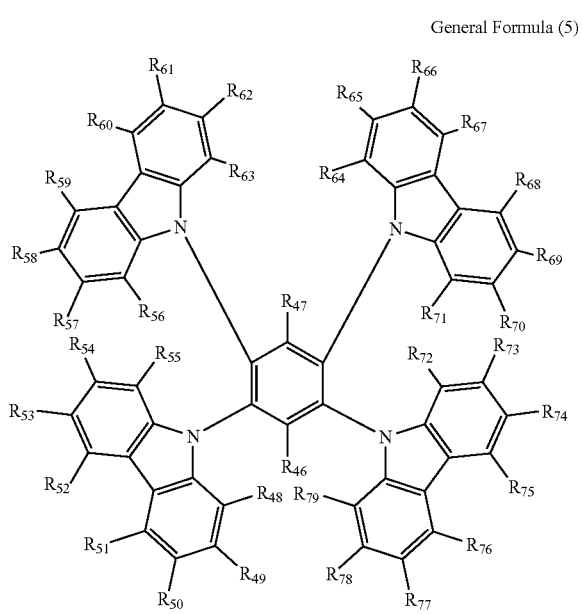

General Formula (4)

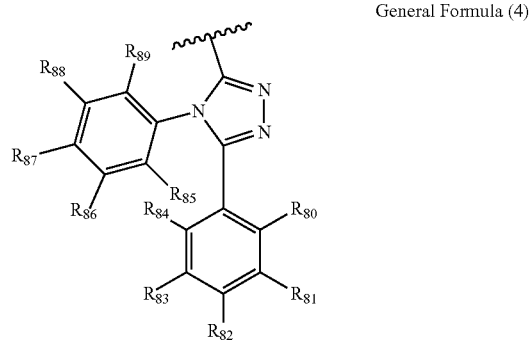

$R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group.

General Formula (2)

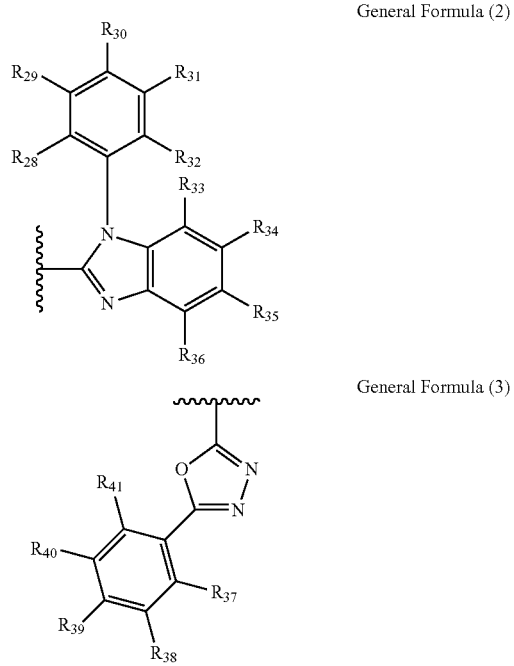

General Formula (3)

$R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group can be selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be a substituted or unsubstituted cycloalkyl group with the carbon number of 3 to 6. The alkoxy group can be selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group can be selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be selected from the group consisting of a substituted or unsubstituted straight-chain silyl group with the carbon number of 1 to 6, and a substituted or unsubstituted branched-chain silyl group with the carbon number of 3 to 6. The alkenyl group can be selected from the group consisting of a substituted or unsubstituted straight-chain alkenyl group with the carbon number of 2 to 6, and a substituted or unsubstituted branched-chain alkenyl group with the carbon number of 3 to 6.

The carbazole derivative of General Formula (5) according to the embodiment can also be the host material of the organic luminescent layer in the organic light-emitting diode. A preferred example is the compound of Chemical Formula (4), o-4Cbz, where $R_{46}$ to $R_{79}$ are all independent hydrogen atoms.

Chemical Formula (4)

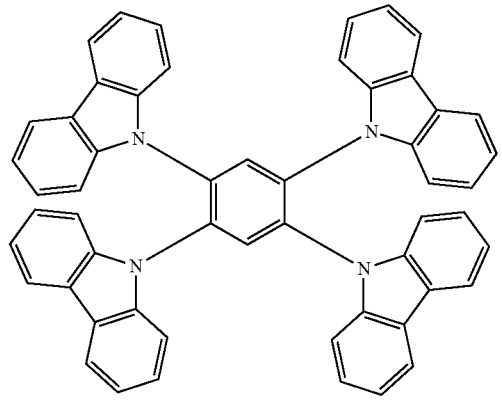

General Formula (3)

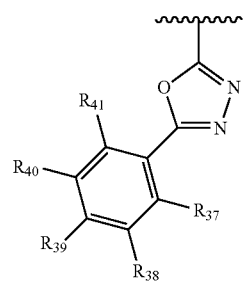

Alternatively, another preferred example is the compound of Chemical Formula (5), o-4CbzBz, where $R_{46}$ is the structure of the following General Formula (2), and $R_{28}$ to $R_{36}$ and $R_{47}$ to $R_{79}$ are all independent hydrogen atoms.

General Formula (2)

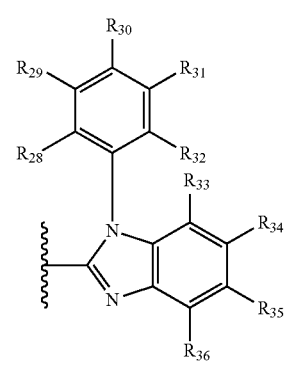

Chemical Formula (6)

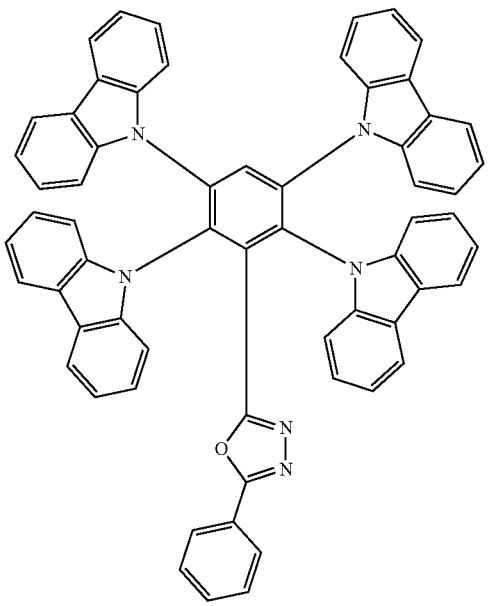

Chemical Formula (5)

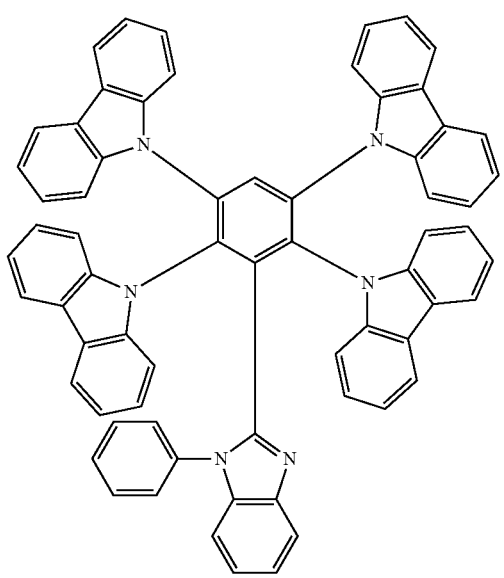

Alternatively, another preferred example is the compound of Chemical Formula (7), o-4CbzTAZ, where $R_{46}$ is the structure of the following General Formula (4) and $R_{47}$ to $R_{89}$ are all independent hydrogen atoms.

General Formula (4)

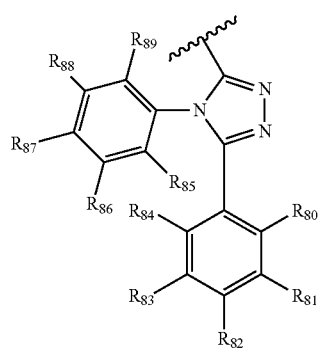

Alternatively, another preferred example is the compound of Chemical Formula (6), o-4CbzOXD, where $R_{46}$ is the structure of the following General Formula (3), and $R_{37}$ to $R_{41}$ and $R_{47}$ to $R_{79}$ are all independent hydrogen atoms, Chemical Formula (7)

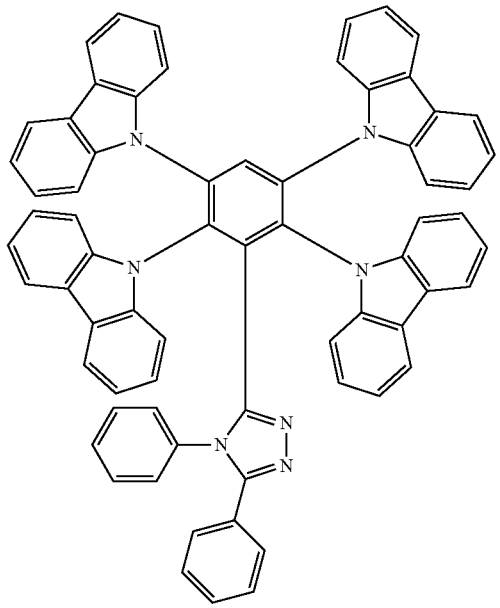

Chemical Formula (9)

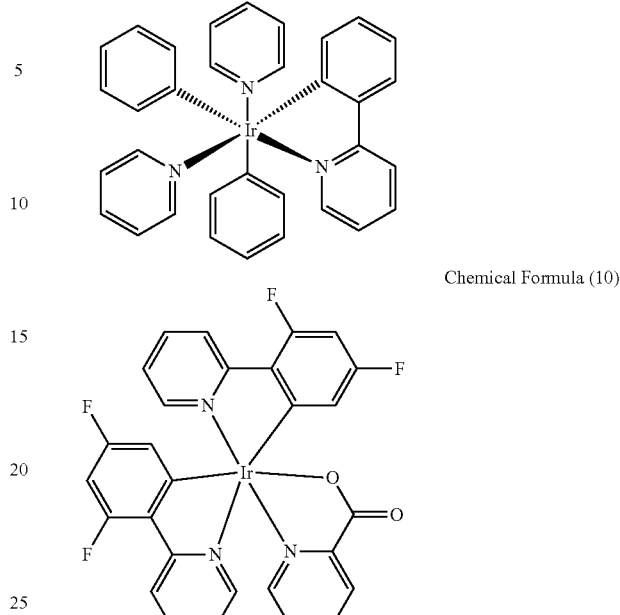

Chemical Formula (10)

In Chemical Formula (1) to (3) and (5) to (7), each structure of General Formula (2) to (4) is functioned as an electron-transporting group, and the carbazole group is functioned as a hole-transporting group. The structures of General Formula (2) to (4) are respectively attached to the single benzene ring at the ortho-position with respect to the position of attachment to the carbazole group, therefore, a series of bipolar host materials of phosphorescent organic light-emitting diodes with high luminous efficiency are synthesized. In other words, the host materials according to the above-mentioned embodiments comprise an electron-transporting group and a hole-transporting group in the same molecule so as to have a characteristic of bipolar carrier-transporting.

In addition, the guest materials for use with the host materials may be any suitable materials applied to the organic luminescent layer of the organic light-emitting diode, for example but not limited to, Ir(2-phq)3, Ir(ppy)3, and FIrpic, and their structures are respectively shown as the following Chemical Formula (8), Chemical Formula (9) and Chemical Formula (10).

Chemical Formula (8)

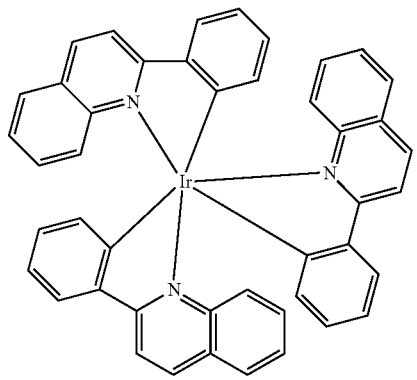

Moreover, in the first and second embodiments, the materials having the structures of General Formula (1) and General Formula (5), in addition to being applied to the organic luminescent layer, can also be applied to any layer of an organic electroluminescent unit, for example, a hole injection layer, hole transport layer, electron blocking layer, electron transport layer or electron injection layer and so on. Herein, the materials having the structures of General Formula (1) and General Formula (5) are especially suitable to be applied to the hole transport layer.

Organic Light-Emitting Diodes

Please refer to FIG. 1, an organic light-emitting diode 100 of the third embodiment according to the invention includes a first electrode layer 120, a second electrode layer 140 and an organic luminescent unit 160. In the embodiment, the first electrode layer 120 can be a transparent electrode material, such as indium tin oxide (ITO), and the second electrode layer 140 can be a metal, transparent conductive substance or any other suitable conductive material. On the other hand, the first electrode layer 120 can also be a metal, transparent conductive substance or any other suitable conductive material, and the second electrode layer 140 can also be a transparent electrode material. Overall, at least one of the first electrode layer 120 and the second electrode layer 140 of the embodiment is a transparent electrode material, so that the light emitted from the organic luminescent unit 160 may pass through the transparent electrode, thereby enabling the organic light-emitting diode 100 to emit light.

In addition, please also refer to FIG. 1, the organic luminescent unit 160 can comprise a hole transport layer 162, an electron blocking layer 164, an organic luminescent layer 166, an electron transport layer 168 and an electron injection layer 169. The electron blocking layer 164, the organic luminescent layer 166 and the electron transport layer 168 are sequentially disposed between the hole transport layer 162 and the electron injection layer 169.

Herein, the materials of the hole transport layer 162 may be 1,1-Bis[4-[N,N'-di(p-tolyl)amino]phenyl]cyclohexane (TAPC), N,N-bis-(1-naphthyl)-N,N-diphenyl-1,1-biphenyl- 4,4-diamine (NPB) or N-N'-diphenyl-N-N'bis(3-methylphenyl)-[1-1'-biphenyl]-4-4'-diamine (TPD) and so on. Moreover, the thickness of the hole transport layer 162 of the embodiment is, for example, less than 100 nm. In the embodiment, the hole transport layer 162 can increase the injection rate of electron holes from the first electrode layer 120 to the organic luminescent layer 166 and can also reduce the driving voltage of the organic light-emitting diode 100.

The materials of the electron blocking layer 164 may be N,N'-dicarbazolyl-3,5-benzene (mCP) or any other material with low electron affinity. In the embodiment, the thickness of the electron blocking layer 164 is, for example, less than 30 nm. The electron blocking layer 164 may further increase the transport rate of the electron hole from the hole transport layer 162 to the organic luminescent layer 166.

In addition, the thickness of the organic luminescent layer 166 of the embodiment is, for example, between 5 nm and 60 nm. The organic luminescent layer 166 includes a host material and a guest material, and the host material can be the above-mentioned carbazole derivative which has a structure of the following General Formula (1).

General Formula (1)

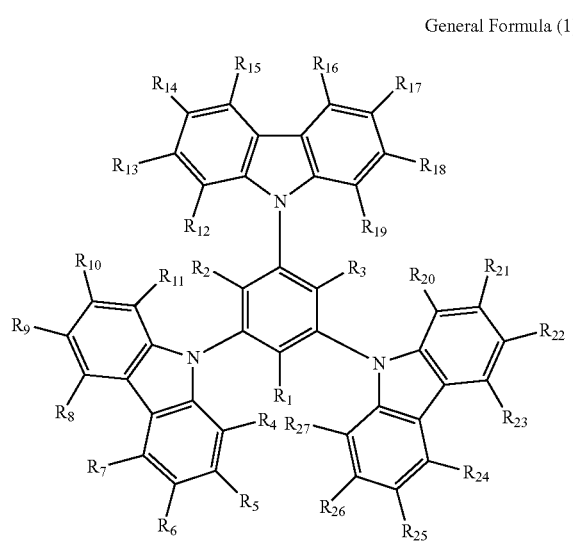

$R_1$ is selected from the group consisting of the structures according to the following General Formula (2), General Formula (3) and General Formula (4).

General Formula (2)

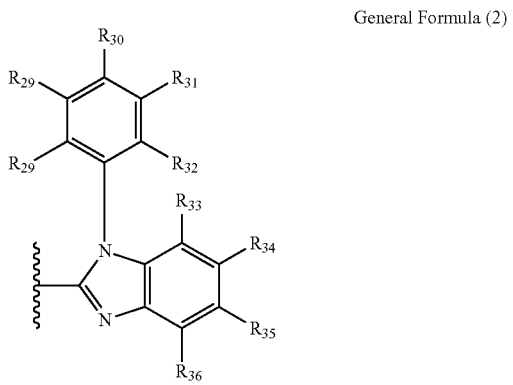

General Formula (3)

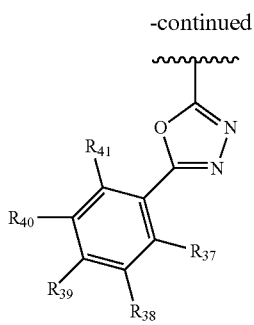

General Formula (4)

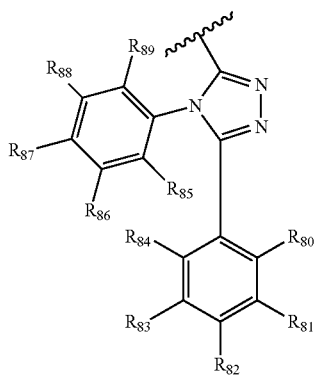

$R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group can be selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be a substituted or unsubstituted cycloalkyl group with the carbon number of 3 to 6. The alkoxy group can be selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group can be selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be selected from the group consisting of a substituted or unsubstituted straight-chain silyl group with the carbon number of 1 to 6, and a substituted or unsubstituted branched-chain silyl group with the carbon number of 3 to 6. The alkenyl group can be selected from the group consisting of a substituted or unsubstituted straight-chain alkenyl group with the carbon number of 2 to 6, and a substituted or unsubstituted branched-chain alkenyl group with the carbon number of 3 to 6, The carbazole derivative of General Formula (1) according to the embodiment can be the host material of the organic luminescent layer in the organic light-emitting diode. A preferred example is the compound of Chemical Formula (1), o-3CbzBz, where $R_1$ is the structure of the following General Formula (2) and $R_2$ to $R_{36}$ are all independent hydrogen atoms.

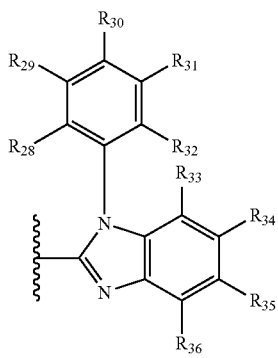

General Formula (2)

Chemical Formula (1)

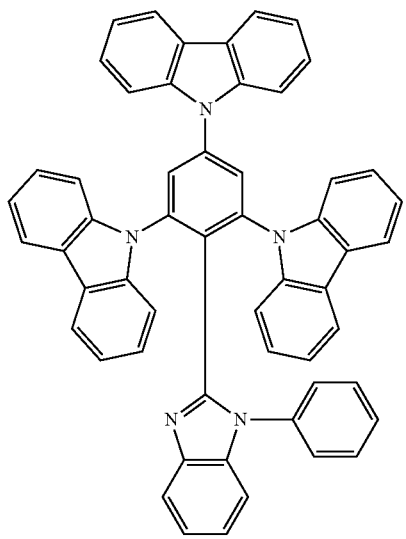

Alternatively, another preferred example is the compound of Chemical Formula (2), o-3CbzOXD, where $R_1$ is the structure of the following General Formula (3), and $R_2$ to $R_{27}$ and $R_{37}$ to $R_{41}$ are all independent hydrogen atoms.

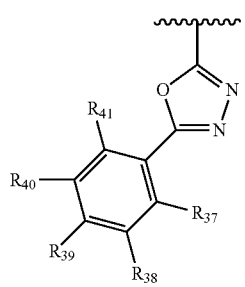

General Formula (3)

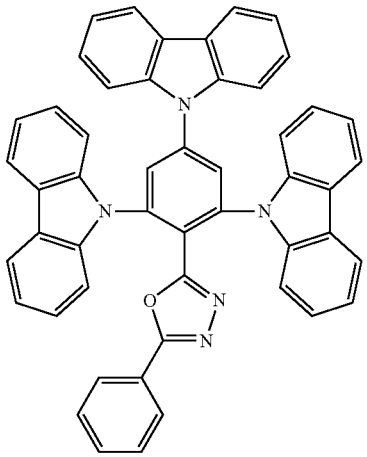

General Formula (2)

Alternatively, another preferred example is the compound of Chemical Formula (3), o-3CbzTAZ, where $R_1$ is the structure of the following General Formula (4), and $R_2$ to $R_{27}$ and $R_{80}$ to $R_{89}$ are all independent hydrogen atoms.

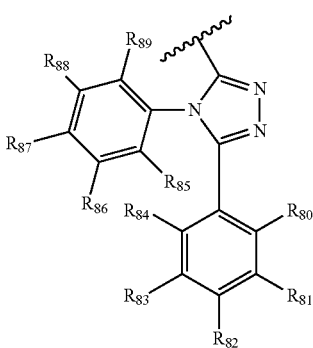

General Formula (4)

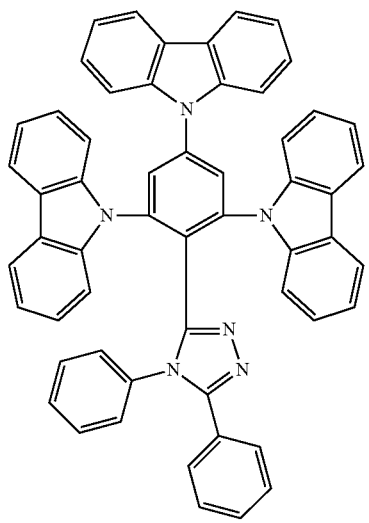

Chemical Formula (3)

In addition, the host material can also be the above-mentioned carbazole derivative which has a structure of the following General Formula (5).

General Formula (5)

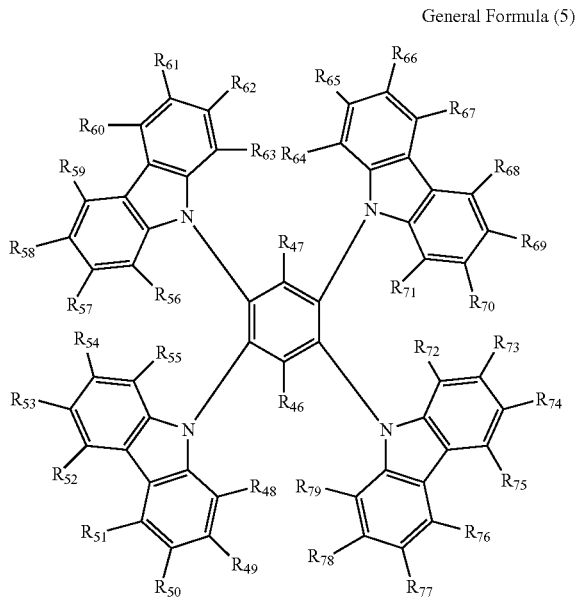

$R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group.

General Formula (2)

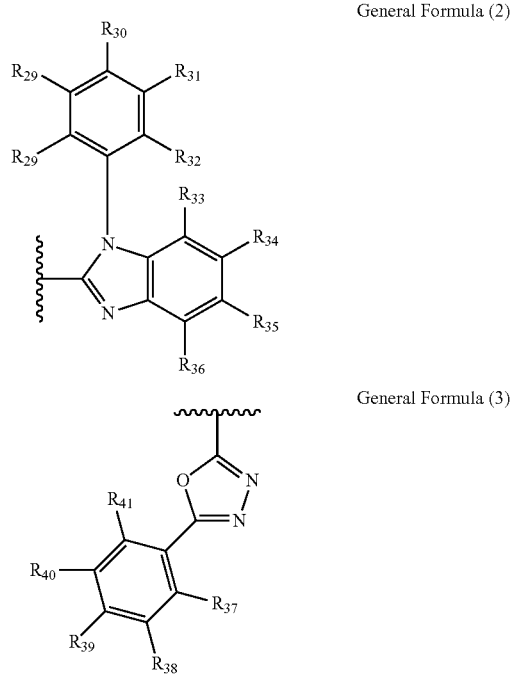

General Formula (3)

General Formula (4)

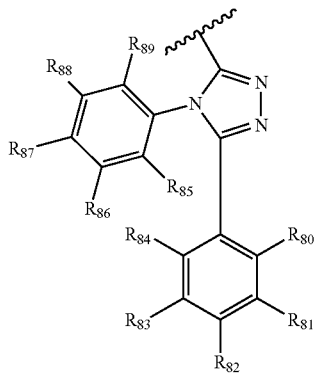

$R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the alkyl group can be selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be a substituted or unsubstituted cycloalkyl group with the carbon number of 3 to 6. The alkoxy group can be selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group can be selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be selected from the group consisting of a substituted or unsubstituted straight-chain silyl group with the carbon number of 1 to 6, and a substituted or unsubstituted branched-chain silyl group with the carbon number of 3 to 6. The alkenyl group can be selected from the group consisting of a substituted or unsubstituted straight-chain alkenyl group with the carbon number of 2 to 6, and a substituted or unsubstituted branched-chain alkenyl group with the carbon number of 3 to 6.

The carbazole derivative of the General Formula (5) according to the embodiment can also be the host material of the organic luminescent layer in the organic light-emitting diode. A preferred example is the compound of Chemical Formula (4), o-4Cbz, where $R_{46}$ to $R_{79}$ are all independent hydrogen atoms.

Chemical Formula (4)

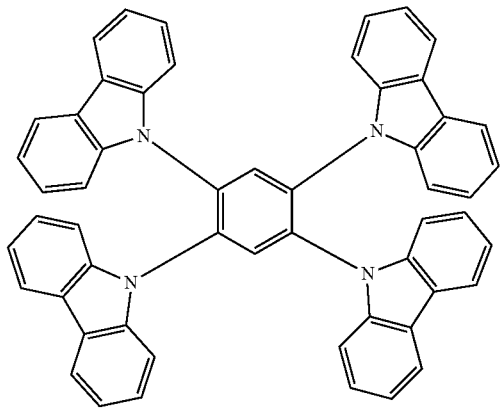

Alternatively, another preferred example is the compound of Chemical Formula (5), o-4CbzBz, where $R_{46}$ is the structure of the following General Formula (2), and $R_{28}$ to $R_{36}$ and $R_{47}$ to $R_{79}$ are all independent hydrogen atoms.

General Fomula (2)

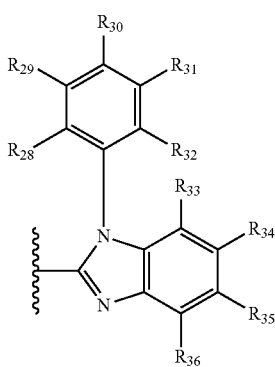

Alternatively, another preferred example is the compound of Chemical Formula (6), o-4CbzOXD, where $R_{46}$ is the structure of the following General Formula (3), and $R_{37}$ to $R_{41}$ and $R_{47}$ to $R_{79}$ are all independent hydrogen atoms.

General Formula (3)

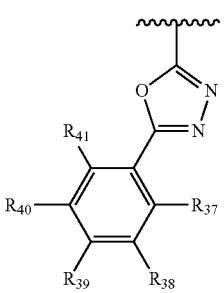

Chemical Formula (6)

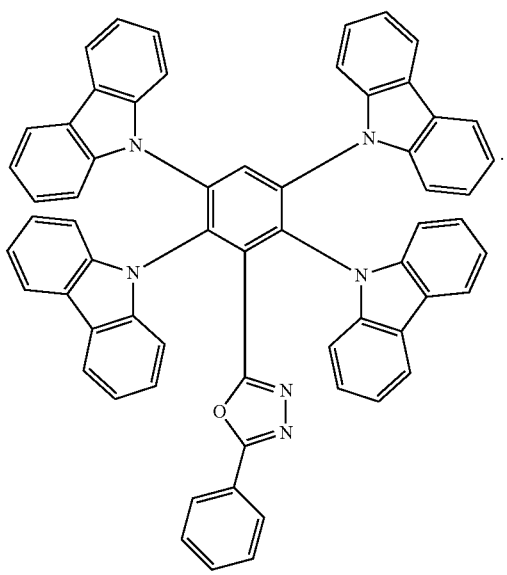

Chemical Formula (5)

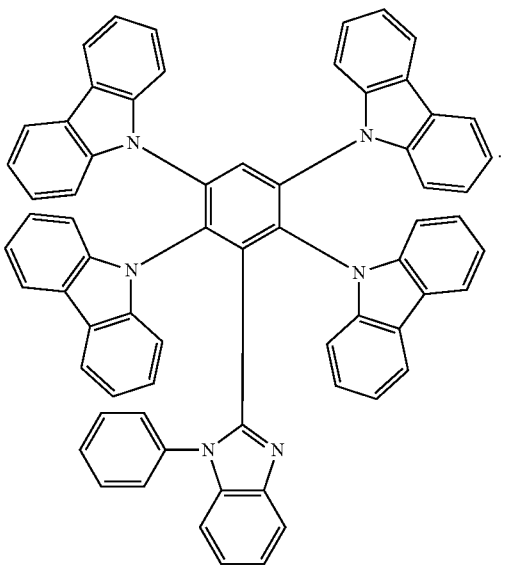

Alternatively, another preferred example is the compound of Chemical Formula (7), o-4CbzTAZ, where $R_{46}$ is the structure of the following General Formula (4) and $R_{47}$ to $R_{89}$ are all independent hydrogen atoms.

General Formula (4)

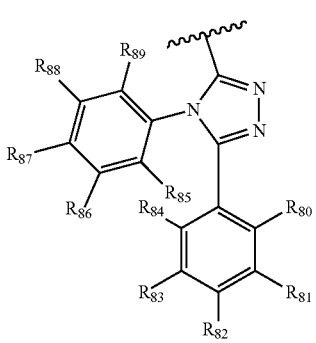

Chemical Formula (7)

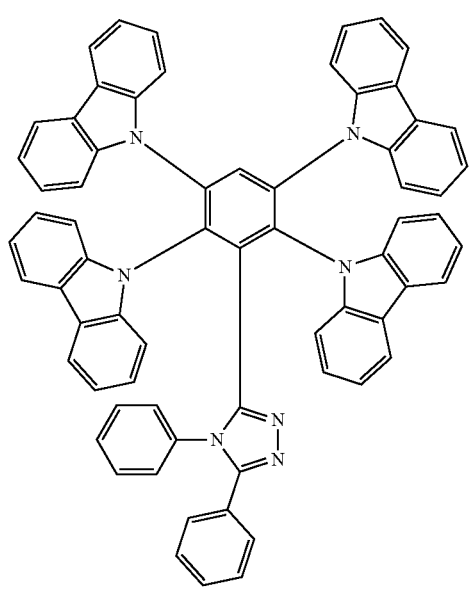

In addition, the content of the host material in the organic luminescent layer 166 is between 60 vol % to 95 vol %. Moreover, the content of the guest material in the organic luminescent layer 166 is between 5 vol % to 40 vol %.

Moreover, the guest materials may be any suitable materials applied to the organic luminescent layer 166, for example but not limited to, Ir(2-phq)3, Ir(ppy)3, and FIrpic, and their structures are respectively shown as the following Chemical Formula (8), Chemical Formula (9) and Chemical Formula (10).

Chemical Formula (8)

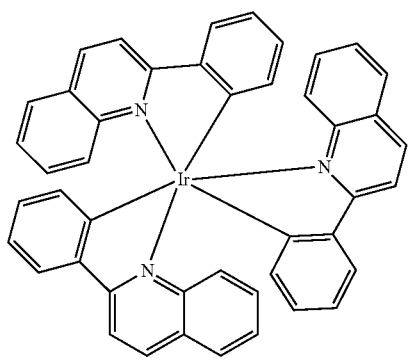

Chemical Formula (9)

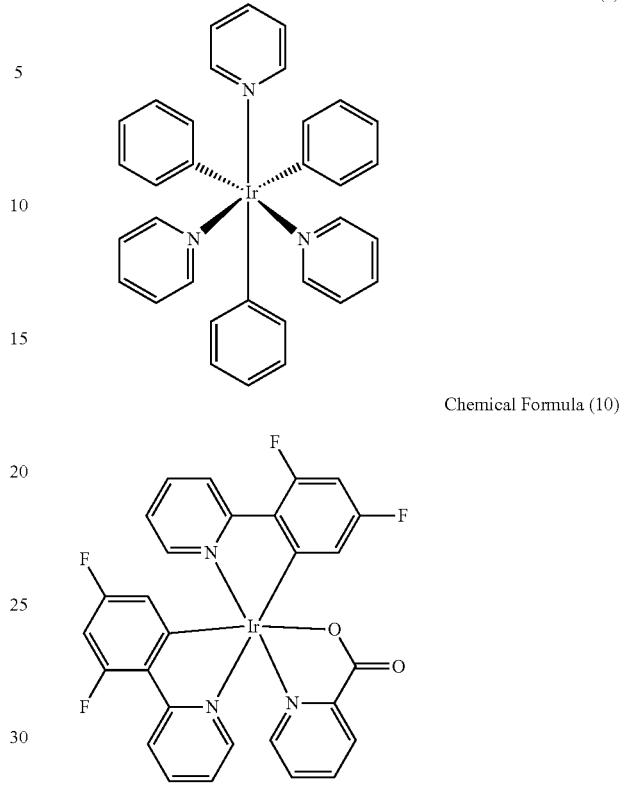

Chemical Formula (10)

In addition, the material of the electron transport layer 168 may be, but not limited to, a metal complex, such as Tris-(8-hydroxy-quinoline)aluminum (Alq$_3$), bis(10-hydroxybenzo-[h]quinolinato)beryllium (BeBq$_2$) and so on, or a heterocyclic compound, such as 2-(4-Biphenylyl)-5-(4-tert-butylphenyl)-1,3,4-oxadiazole (PBD), 3-(4-Biphenylyl)-4-phenyl-5-tert-butylphenyl-1,2,4-triazole (TAZ), 2,2', 2"-(1,3,5 -Benzinetriyl)-tris(1-phenyl-1-H-benzimidazole) (TPBI), diphenylbis(4-(pyridin-3-yl)phenyl)silane (DPPS), 3,3'-[5'-[3-(3-Pyridinyl)phenyl] [1,1':3',1"-terphenyl]-3,3"-diyl]bispyridine (TmPyPB) and so on. In the embodiment, the thickness of the electron transport layer 168 may be, for example, less than 100 nm. The electron transport layer 168 can facilitate the transfer of electrons from the second electrode layer 140 to the organic luminescent layer 166 to increase the transport rate of the electron. Moreover, the material of the electron injection layer 169 may be, for example, LiF. The thickness of the electron injection layer 169 may be, for example, 0.9 nm.

Figure 2:
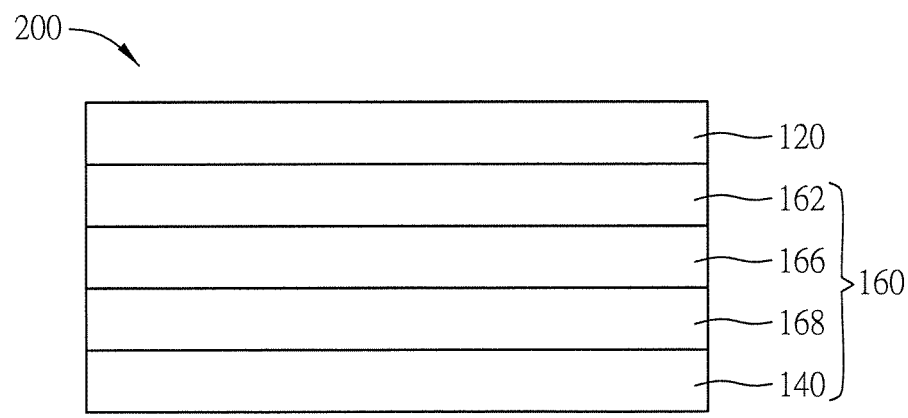
FIG. 2 is a cross-sectional schematic diagram of an organic light-emitting diode of the fourth embodiment according to the invention.

In addition, FIG. 2 is a cross-sectional schematic diagram of an organic light-emitting diode 200 of the fourth embodiment according to the invention. The configuration of the organic light-emitting diode 200 is substantially similar with that of the organic light-emitting diode 100, and same elements have substantial the same characteristics and functions. Therefore, the similar references relate to the similar elements, and detailed explanation is omitted hereinafter.

Please refer to FIG. 2, in the embodiment, the organic luminescent unit 160 can comprise a hole transport layer 162, an organic luminescent layer 166 and an electron transport layer 168. The organic luminescent layer 166 is disposed between the hole transport layer 162 and the electron transport layer 168.

Figure 3:
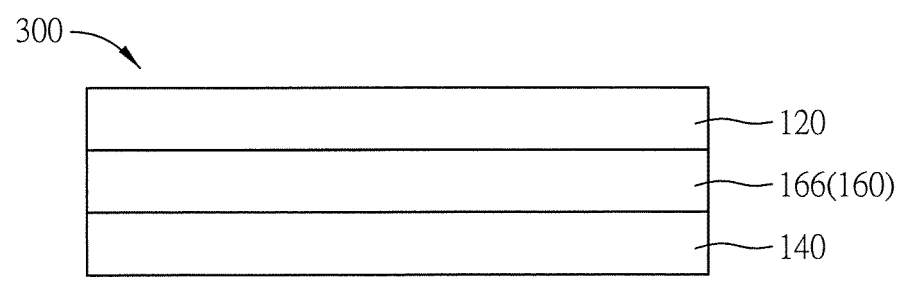
FIG. 3 is a cross-sectional schematic diagram of an organic light-emitting diode of the fifth embodiment according to the invention.

In addition, FIG. 3 is a cross-sectional schematic diagram of an organic light-emitting diode 300 of the fifth embodiment according to the invention. The configuration of the organic light-emitting diode 300 is substantially similar with that of the organic light-emitting diode 100, and same elements have substantial the same characteristics and functions. Therefore, the similar references relate to the similar elements, and detailed explanation is omitted hereinafter.

Please refer to FIG. 3, in the embodiment, the organic luminescent unit 160 can comprise an organic luminescent layer 166.

The configuration of the organic light-emitting diode according to the invention is not limited to what is disclosed in the third, fourth or fifth embodiment. The third, fourth and fifth embodiments are embodiments for illustration, In the above-mentioned third, fourth and fifth embodiments, the materials having the structures of General Formula (1) and General Formula (5), in addition to being applied to the organic luminescent layer, can also be applied to any layer of an organic electroluminescent unit, for example, a hole injection layer, hole transport layer, electron blocking layer, electron transport layer or electron injection layer and so on. Herein, the materials having the structures of General Formula (1) and General Formula (5) are especially suitable to be applied to the hole transport layer.

To illustrate the synthesis of Chemical Formula (1) to Chemical Formula (7), there are several examples shown below.

EXAMPLE 1

Synthesis of Chemical Formula (1) (Compound o-3CbzBz)

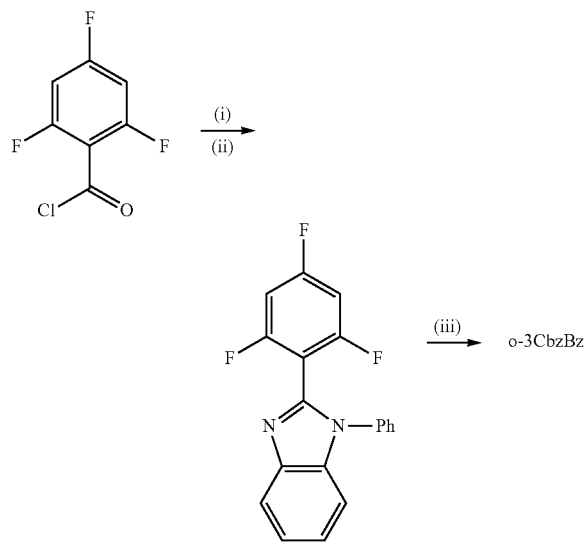

(i): 2-aminodiphenylamine, triethylamine (TEA) and dichloromethan (DCM)
(ii): acetic acid (AcOH), refluxed
(iii): carbazole (Cbz), $Cs_2CO_3$, dimethyl sulfoxide (DMSO), 160° C., under Argon 2,4,6-trifluorobenzoyl chloride (0.97 g, 4.98 mmol) was dissolved in dichloromethane (6 mL) and added slowly a solution of triethylamine (1.4 mL) and 2-aminodiphenylamine (1.01 g, 5.48 mmol) in dichloromethane (6 mL). The mixture was reacted for 12 hours. Then, the mixture was washed with $H_2O$ (20 mL*1), and neutralized with 1N HCl (20 mL*2). The organic layer was dried with anhydrous $MgSO_4$ and concentrated to give a crude intermediate that was subjected to dehydrative cyclization in refluxing AcOH (20 mL) for 24 hours. The solvent was then removed by vacuum distillation to get a crude that was dissolved again in dichloromethane and washed with 0.5 M $K_2CO_{3(aq)}$ twice. The organic layer was collected, dried with anhydrous $MgSO_4$, concentrated, and purified by liquid column chromatography on silica gel with EtOAc/DCM=1/30 as eluent to obtain a white powder 1 (1.31 g, yield:81%). Spectral data as follow: m.p. 162-163° C.; $^1$H NMR (400 MHz, $CD_2Cl_2$): d 7.88-7.86 (m, 1H), 7.49-7.29 (m, 8H), 7.75-7.68 (m, 2H); $^{13}$C NMR (100 MHz, $CD_2Cl_2$): d 165.79 (m), 163.28 (m), 160.71 (m), 143.95, 142.28, 136.87, 136.24, 130.20, 129.27, 126.99, 124.48, 123.51, 120.74, 111.17, 101.23 (m); HRMS calcd for $C_{19}H_{12}F_3N_2$ ($M^+$) 325.0953, obsd. 325.0943. Anal. Calcd for $C_{19}H_{11}F_3N_2$: C, 70.37; H, 3.42; N, 8.64; Found C, 70.45; H, 3.68; N, 8.48.

A mixture of $Cs_2CO_3$ (1.47 g, 4.51 mmol), carbazole (0.52 g, 3.11 mmol) and the white powder 1 (0.32 g, 0.99 mmol) in dimethyl sulfoxide (2.5 mL, 0.4 M) was reacted at 160 □ under an argon system for 24 hours. After the reaction, the mixture was diluted with $H_2O$ and filtered to get a yellow crude. The yellow crude was purified through by liquid column chromatography on silica gel with hexane/DCM=1/2 as eluent to obtain compound o-3CbzBz (0.66 g, yield: 87%) as a white powder. The white powder o-3CbzBz was purified by recrystallization from DCM/EtOH. The white powder o-3CbzBz was sublimed twice under thermal evaporation and deposition conditions before device fabrication. Spectral data as follow: m.p. 314-315° C.; $^1$H NMR (400 MHz, $CD_2Cl_2$): d 8.10 (d, J=7.68, 2H), 8.03 (d, J=7.44, 4H), 7.92 (s, 2H), 7.84 (d, J=8.24, 2H), 7.63 (d, J=8.20, 2H), 7.47-7.40 (m, 4H), 7.31-7.18 (m, 9H), 7.10-6.95 (m, 6H), 6.88 (t, J=7.72, 1H), 6.67 (d, J=8.08, 1H), 6.54 (d, J =7.60, 2H); $^{13}$C NMR (100 MHz, $CD_2Cl_2$):d 145.82, 143.18, 142.56, 142.43, 142.19, 141.83, 140.38, 136.03, 135.46, 129.68, 129.24, 128.77, 127.94, 126.97,126.49, 126.34, 126.02, 124.80, 124.61, 124.10, 123.72, 122.74, 121.60, 121.06, 120.98, 120.88, 120.76, 120.26, 120.11, 112.78, 110.68, 110.32, 110.28; HRMS calcd for $C_{55}H_{35}N_5$ ($M^+$) 766.2971, obsd. 766.2960. Anal. Calcd for $C_{55}H_{35}N_5$: C, 86.25; H, 4.61; N, 9.14; Found C, 86.10; H, 4.63; N, 9.12.

EXAMPLE 2

Synthesis of Chemical Formula (2) (Compound o-3CbzOXD)

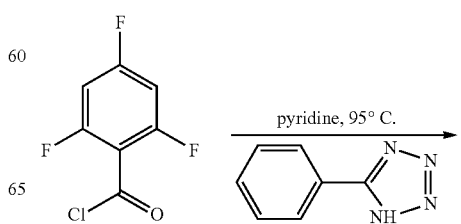

EXAMPLE 3

Synthesis of Chemical Formula (3) (Compound o-3CbzTAZ)

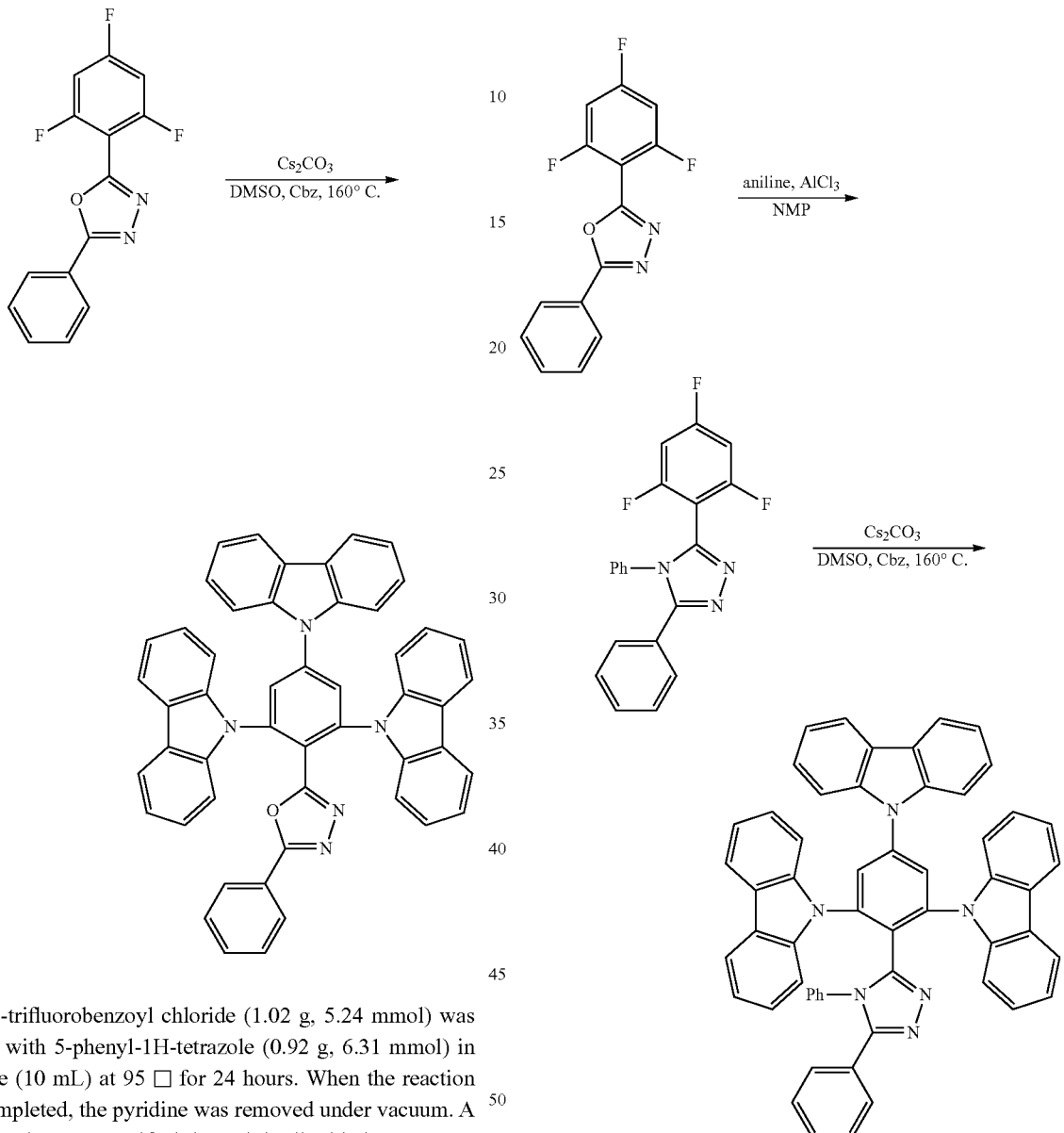

2,4,6-trifluorobenzoyl chloride (1.02 g, 5.24 mmol) was reacted with 5-phenyl-1H-tetrazole (0.92 g, 6.31 mmol) in pyridine (10 mL) at 95 ☐ for 24 hours. When the reaction was completed, the pyridine was removed under vacuum. A crude product was purified through by liquid chromatography on silica gel with dichloromethane as the eluent to obtain a white solid 2.

A mixture of $Cs_2CO_3$ (1.47 g, 4.51 mmol), carbazole (0.52 g, 3.11 mmol) and the white solid 2 (0.27 g, 0.99 mmol) in dimethyl sulfoxide (2.5 mL, 0.4 M) was reacted at 160 ☐ under an argon system for 24 hours. After the reaction, the mixture was diluted with $H_2O$ and filtered to get a yellow crude. The yellow crude product was collected as a solid and purified by recrystallization from dichloromethane and acetone to afford compound o-3CbzOXD. Compound o-3CbzOXD was sublimed twice under thermal evaporation and deposition conditions before device fabrication.

A mixture of aniline (1.10 ml, 12.0 mmol) and aluminum trichloride (0.40 g, 3.00 mmol) was stirred at 140 ☐ under an argon system for 2 to 2.5 hours. The white solid 2 (2.01 g, 7.28 mmol) in N-Methyl-2-pyrrolidone (1 ml) was added to the above mixture, and then heated at 200 ☐ for 7 to 10 hours. The reaction mixture was poured into ice water and the precipitated crude product was collected and dried. Since the conversion is incomplete in the first run, the crude mixture was re-subjected to the reaction. After the second run of the reaction, the crude product was collected and purified by recrystallization from dichloromethane and ethyl acetate to obtain a product 3.

A mixture of $Cs_2CO_3$ (1.47 g, 4.51 mmol), carbazole (0.52 g, 3.11 mmol) and the product 3 (0.35 g, 0.99 mmol) in dimethyl sulfoxide (2.5 mL, 0.4 M) was reacted at 160 □ under an argon system for 24 hours. After the reaction, the mixture was diluted with H₂O and filtered to get a yellow crude. The yellow crude product collected as a solid and purified by recrystallization from dichloromethane and acetone to afford compound o-3CbzTAZ. Compound o-3CbzTAZ was sublimed twice under thermal evaporation and deposition conditions before device fabrication.

EXAMPLE 4

Synthesis of Chemical Formula (4) (Compound o-4Cbz)

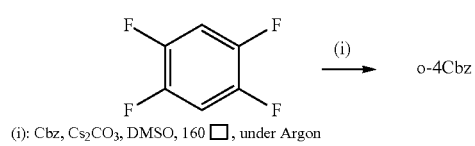

(i): Cbz, Cs₂CO₃, DMSO, 160 □, under Argon

A mixture of Cs₂CO₃ (11.70 g, 35.90 mmol), carbazole (4.21 g, 25.17 mmol) and 1,2,4,5-tetrafluorobenzene (0.90 g, 6.00 mmol) in dimethyl sulfoxide (15 mL, 0.4 M) was reacted at 160 □ under an argon system for 24 hours. After the reaction, the mixture was diluted with 300 mL H₂O and filtered to get a yellow crude. The yellow crude was washed sequentially by methanol, ethyl acetate and acetone to obtain compound o-4Cbz (3.98 g, yield: 97%) as a white powder. Spectral data as follow: m.p.>400° C.; ¹H NMR (400 MHz, CD₂Cl₂): d 8.37 (s, 2H), 7.88 (d, J=7.2, 8H), 7.45 (d, J=7.72, 8H), 7.18-7.10 (m, 16H); ¹³C NMR (100 MHz, CD₂Cl₂):d 140.23, 135.12, 135.28, 126.36, 124.27, 121.07, 120.66, 110.38; HRMS calcd for C₅₄H₃₅N₄ (M⁺) 739.2862, obsd. 739.2833. Anal. Calcd for C₅₄H₃₄N₄: C, 87.78; H, 4.64; N, 7.58; Found C, 87.69; H, 4.64; N, 7.57.

EXAMPLE 5

Synthesis of Chemical Formula (5) (Compound o-4CbzBz)

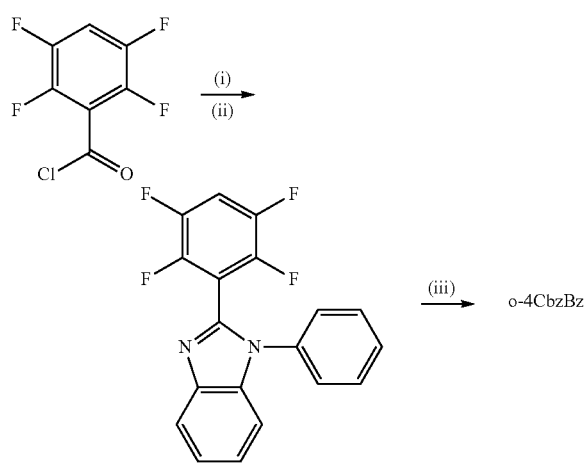

(i): 2-aminodiphenylamine, TEA, dichloromethan
(ii): AcOH, refluxed
(iii): Cbz, Cs₂CO₃, DMSO, 160° C., under Argon 2,3,5,6-Tetrafluorobenzoyl chloride (2.83 g, 13.34 mmol) was dissolved in dichloromethane (35 mL) and added slowly a solution of triethylamine (3.7 mL) and 2-aminodiphenylamine (2.70 g, 14.67 mmol) in dichloromethane (35 mL). The mixture was reacted for 12 hours. Then, the mixture was washed with H₂O (70 mL*1) and neutralized with 1N HCl (70 mL*2). The organic layer was dried with anhydrous MgSO₄ and concentrated to give a crude intermediate that was subjected to dehydrative cyclization in refluxing AcOH (70 mL) for 24 hours. The solvent was then removed by vacuum distillation to get a crude that was dissolved again in DCM and washed with 1M K₂CO₃$_{(aq)}$ (100 mL*2). The organic layer was collected, dried with anhydrous MgSO₄, concentrated, and the crude was purified by recrystallization with DCM/hexane to obtain a colorless product 4 (3.73 g, yield: 81%). Spectral data as follow: m.p. 153-154° C.; ¹H NMR (400 MHz, d-DMSO): d 8.15-8.06 (m, 1H), 7.90-7.88 (m, 1H), 7.57-7.48 (m, 3H), 7.41-7.39 (m, 5H); ¹³C NMR (100 MHz, d-DMSO): d 146.51 (m), 145.07 (m), 144.11 (m), 142.66, 139.63, 135.51, 134.55, 129.97, 129.08, 126.03, 124.57, 123.30, 120.06, 110.83, 109.47 (m); HRMS calcd for C₁₉H₁₁F₄N₂ (M⁺) 343.3046, obsd. 343.0864 Anal. Calcd for C₁₉H₁₀F₄N₂: C, 66.67; H, 2.94; N, 8.18; Found C, 66.59; H, 2.95; N, 8.18.

A mixture of Cs₂CO₃ (13.65 g, 41.90 mmol), carbazole (4.80 g, 28.70 mmol) and the colorless product 4 (2.38 g, 6.95 mmol) in dimethylacetamide (DMAc, 17.5 mL, 0.4 M) was reacted at 160 □ under an argon system for 24 hours. After the reaction, the mixture was diluted with H₂O (350 ml) and filtered to get a yellow crude. The yellow crude has poor solubility to any solvent. Sequentially washed the yellow crude with EtOAc, MeOH and acetone to afford compound o-4CbzBz (5.85 g, 90%) as a white powder. Compound o-4CbzBz was sublimed twice under thermal evaporation and deposition conditions before device fabrication. Spectral data as follow: m.p.>400° C.; ¹H NMR (500 MHz, CD₂Cl₂): d 8.28 (s, 1H), 8.02 (d, J=8.25, 2H), 7.82 (d, J=7.05, 2H), 7.73 (d, J=8.15, 2H), 7.68-7.65 (m, 4H), 7.51 (d, J=7.3, 2H), 7.45 (t, J=7.10, 2H), 7.38 (t, J=7.12, 2H), 7.21-7.17 (m, 3H), 7.09 (t, J =7.3, 2H), 7.01-6.99 (m, 3H), 6.92-6.88 (m, 5H), 6.83 (t, J =4.07, 1H), 6.75-6.71 (m, 4H), 6.65 (d, J =8.25, 2H), 6.60 (d, J =8.05, 1H), 6.55-6.51 (m, 4H); ¹³C NMR (100 MHz, CD₂Cl₂):d 145.01, 142.64, 140.98, 140.73, 139.89, 139.85, 138.17, 137.50, 136.31, 135.73, 135.18, 134.66, 129.61, 128.65, 126.34, 125.61, 125.57, 125.45, 124.98, 124.37, 124.26, 124.08, 123.76, 123.73, 122.69, 121.09, 120.73, 120.71, 120.29, 119.97, 119.75, 119.64, 113.49, 110.97, 110.80, 110.73, 110.20; HRMS calcd for C₆₇H₄₃N₆ (M⁺) 931.3549, obsd. 931.3931. Anal. Calcd for C₆₇H₄₂N₆: C, 86.43; H, 4.55; N, 9.03; Found C, 86.39; H, 4.52; N, 9.02.

EXAMPLE 6

Synthesis of Chemical Formula (6) (Compound o-4CbzOXD)

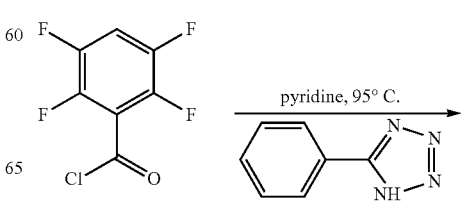

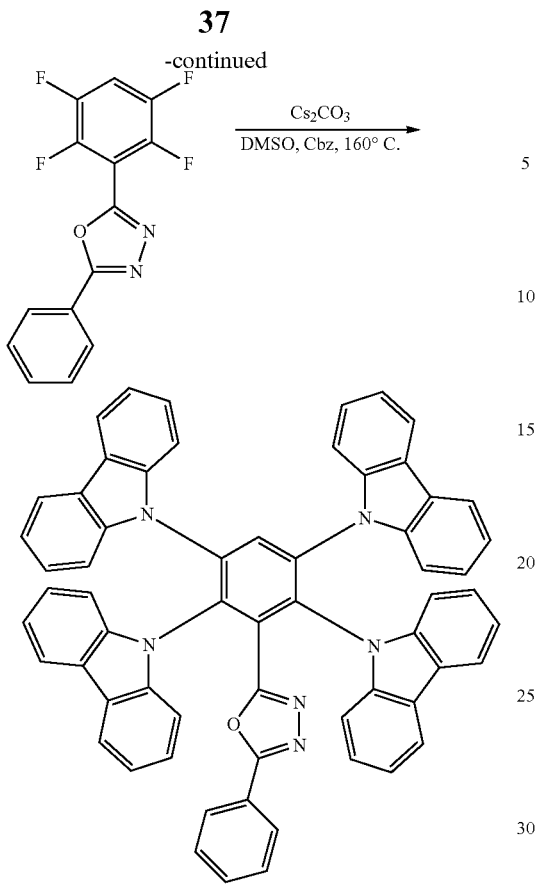

2,3,5,6-Tetrafluorobenzoyl chloride (1.11 g, 5.24 mmol) was reacted with 5-phenyl-1H-tetrazole (0.92 g, 6.31 mmol) in pyridine (10 mL) at 95 □ for 24 hours. When the reaction was completed, the pyridine was removed under vacuum. The crude product was purified through by liquid column chromatography on silica gel with dichloromethane as the eluent to obtain a white solid 5.

A mixture of $Cs_2CO_3$ (13.65 g, 41.90 mmol), carbazole (4.80 g, 28.70 mmol) and the white solid 5 (2.04 g, 6.95 mmol) in DMSO (17.5 mL, 0.4 M) was reacted at 160 □ under an argon system for 24 hours. After the reaction, the mixture was diluted with $H_2O$ (350 ml) and filtered to get a yellow crude. The yellow crude has poor solubility to any solvent. Sequentially washed the yellow crude with EtOAc, MeOH and acetone to afford compound o-4CbzOXD as a white powder. Compound o-4CbzOXD was sublimed twice under thermal evaporation and deposition conditions before device fabrication.

EXAMPLE 7

Synthesis of Chemical Formula (7) (Compound o-4CbzTAZ)

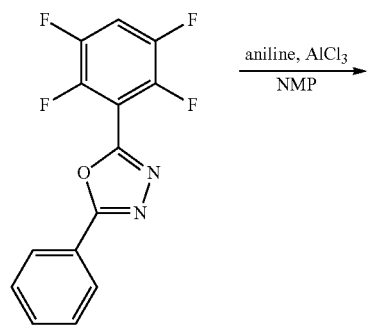

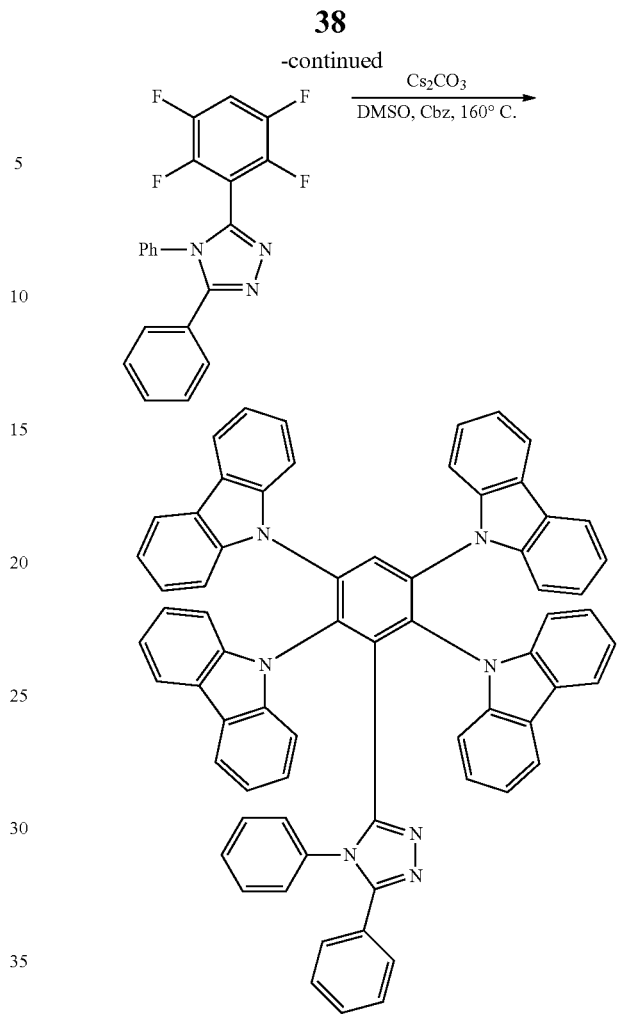

A mixture of aniline (1.10 ml, 12.0 mmol) and aluminum trichloride (0.40 g, 3.00 mmol) was stirred at 140 □ under an argon system for 2 to 2.5 hours. The white solid 5 (2.14 g, 7.28 mmol) in N-Methyl-2-pyrrolidone (NMP, 1 ml) was added to the above mixture, and then heated at 200 □ for 7 to 10 hours. The reaction mixture was poured into ice water and the precipitated crude product was collected and dried. Since the conversion is incomplete in the first run, the crude mixture was re-subjected to the reaction. After the second run of the reaction, the crude product was collected and purified by recrystallization from $CH_2Cl_2$ and EtOAc to obtain a product 6.

A mixture of $Cs_2CO_3$ (13.65 g, 41.90 mmol), carbazole (4.80 g, 28.70 mmol) and the product 6 (2.56 g, 6.95 mmol) in DMSO (17.5 mL, 0.4 M) was reacted at 160 □ under an argon system for 24 hours. After the reaction, the mixture was diluted with $H_2O$ (350 ml) and filtered to get a yellow crude. The yellow crude has poor solubility to any solvent. Sequentially washed the yellow crude with EtOAc, MeOH and acetone to obtain a compound o-4CbzTAZ as a white powder. Compound o-4CbzTAZ was sublimed twice under thermal evaporation and deposition conditions before device fabrication.

Evaluation Methods for the Host Material

The host material includes the compound which is mentioned above from Example 1, Example 4 and Example 5 (i.e., Chemical Formula (1), Chemical Formula (4) and Chemical Formula (5)). The evaluation method for the host material is to perform the measurements of the triplet energy level (ET), the glass transition temperature (Tg), the pyrolysis temperature (Td), the highest occupied molecular orbital (HOMO), and the lowest unoccupied molecular orbital (LUMO) on the above-mentioned compound of examples, respectively. The triplet energy level measured at low temperature by spectrometer is the basis of selecting the host material of phosphorescent emitter. For blue light-emitting diode, FIrpic (ET=2.65 eV) is a common phosphorescent emitter and the ET of the host emitter used with FIrpic should be higher than 2.65 eV to avoid low luminous efficiency caused by reverse energy transfer. The glass transition temperature and the pyrolysis temperature respectively measured by differential scanning calorimeter (DSC) and thermogravimetric analyzer (TGA) are considered to be the basis of the stability for the fabrication and performance of unit. HOMO and LUMO are acquired receptively from oxidation potential and reduction potential of the material by using cyclic voltammetry, which can facilitate in searching of an electric charge injection material with small difference energy gap and enhance the efficiency of the unit. The properties of the compounds of Chemical Formula (1) o-3CbzBz, Chemical Formula (4) o-4Cbz and Chemical Formula (5) o-4CbzBz are shown in Table 1.

TABLE 1

| Compound | $E_T$ (eV) | $T_g$ (□) | $T_d$ (□) | HOMO (eV) | LUMO (eV) |
|---|---|---|---|---|---|
| Chemical Formula (1) | 3.1 | 150 | 383 | 5.8 | 2.3 |
| Chemical Formula (4) | 3.1 | N.A. | 468 | 5.8 | 2.4 |
| Chemical Formula (5) | 2.8 | N.A. | 478 | 5.7 | 2.5 |

According to Table 1, the pyrolysis temperatures of the compound of Chemical Formula (1) o-3CbzBz, Chemical Formula (4) o-4Cbz and Chemical Formula (5) o-4CbzBz are all higher than 350 □. It is because that their structures contain multiple benzene rings which are rigid structures, so that the pyrolysis caused by the heat is not easily occurred during the heating process. Based on the result mentioned above, these derivatives can have fine thermal stability and high triplet energy level and are quite beneficial to be the host material in the organic luminescent layer of the organic light emitting diode.

$T_g$ is another index of evaluating the stability of the unit. The material with high $T_g$ has good performance on the stability of the unit. As shown in Table 1, comparing with commercial material TCP ($T_g$: 125 □), the performance on thermal property Tg of o-3CbzBz is superior to that of TCP. Thus, benzimidazole group can improve the thermal stability is confirmed. In addition, the glass transition temperature of o-4Cbz and o-4CbzBz can not be observed since the heating temperature of the experimental equipment can not reach to the melting points of o-4Cbz and o-4CbzBz ($T_g$ are higher than 400 □). Accordingly, the molecular can not be transformed into the amorphous state and $T_g$ can not be measured.

The Efficiency of Compounds (Chemical Formula (1), Chemical Formula (4) and Chemical Formula (5)) Which Were Used as Host Materials in Organic Light-Emitting Diodes The unit structure is ITO/TAPC(50 nm)/mCP(10 nm)/host:emitter(30 nm)/DPPS(30 nm)/LiF(0.9 nm)/Al(120 nm). The host materials of the organic luminescent layer are based on the compound of Chemical Formula (1), Chemical Formula (4) and Chemical Formula (5). The host materials were mixed with the guest material at various ratio of emitter (FIrpic). Herein, the material of the first electrode layer of the organic light-emitting diode is ITO. The material of the second electrode layer is aluminum with the thickness of 120 nm. The material of the hole transport layer is TAPC with the thickness of 50 nm. The thickness of the organic luminescent layer is 30 nm. The material of the electron blocking layer is mCP with the thickness of 10 nm. The material of the electron transport layer is DPPS with the thickness of 30 nm. The material of electron injecting layer is LiF with the thickness of 0.9 nm. The above-mentioned layers are made by vapor deposition to form the organic light-emitting diodes of the embodiment, and the driving voltage (V) under 1 cd/m$^2$, the maximum current efficiency CE (cd/A), the maximum power efficiency PE (1 m/W), and the maximum external quantum efficiency (EQE; %) of the organic light-emitting diodes are measured. The results are shown in Table 2.

TABLE 2

| Unit [a] | driving voltage (V) | maximum current efficiency (cd/A) | power efficiency (lm/W) | EQE (%) |
|---|---|---|---|---|
| Chemical Formula (1) -6% | 3.5 | 58.22 | 59.40 | 27.96 |
| Chemical Formula (4) -6% | 3.5 | 52.07 | 47.36 | 25.16 |
| Chemical Formula (5) -15% | 3.5 | 43.69 | 39.29 | 18.82 |

[a] the doping concentration of FIrpic

The organic light-emitting diodes shown in Table 2 not only have low driving voltages but also have the fine current efficiency, power efficiency and external quantum efficiency. Accordingly, the host materials of the present invention have high transmission rate of electrons and electron holes, and are not necessarily to be operated under high driving voltage. Also, the external quantum efficiencies of the host materials shown in Table 2 are high as well. Consequently, the host materials of the present invention have higher triplet energy level, which is beneficial to reduce reverse energy transfer and to increase the luminous efficiency of the organic light-emitting diode.

Comparison of the Efficiency of Compounds (Chemical Formula (4) and mCP) Which Were Used as Hole Transport Layers in Organic Light-Emitting Diodes The unit structure is ITO/TAPC(500 nm)/o-4Cbz(50 to 200 nm)/host:emitter(300 nm):15%)/DPPS(500 nm)/LiF/Al. The host materials of the organic luminescent layer are based on the compound of Chemical Formula (5). Herein, the material of the first electrode layer of the organic light-emitting diode is ITO. The material of the second electrode layer is aluminum with the thickness of 120 nm. The material of the first hole transport layer is TAPC with the thickness of 500 nm. The material of the second hole transport layer is o-4Cbz or mCP with the thickness of 50 to 200 nm. The thickness of the organic luminescent layer is 300 nm. The material of the electron transport layer is DPPS with the thickness of 500 nm. The material of electron injecting layer is LiF with the thickness of 0.9 nm. The above-mentioned layers are made by vapor deposition to form the organic light-emitting diodes of the embodiment. The results of evaluation are shown in Tables 3 and 4.

TABLE 3

| Unit | driving voltage @20 mA | current efficiency (J) @1000 nits | Maximum brightness |
|---|---|---|---|
| Chemical Formula (4) -100 nm | 6.93 | 1.68 | 18600@10 V |
| Chemical Formula (4) -150 nm | 7.32 | 1.67 | 18760@10.5 V |
| Chemical Formula (4) -200 nm | 7.70 | 1.68 | 18180@11 V |
| mCP -100 nm | 7.19 | 1.70 | 20340@10 V |

TABLE 4

| Unit | Current efficiency | | Power efficiency (lm/W) | | EQE (%) | |
|---|---|---|---|---|---|---|
| | Maximum | @1000 nits | Maximum | @1000 nits | Maximum | @1000 nits |
| Chemical Formula (4) –100 nm | 62.68 @3.5 V | 59.66 | 65.8 @3 V | 39.28 | 30.23 | 28.86 |
| Chemical Formula (4) –150 nm | 64.09 @3.5 V | 60.33 | 66.3 @3 V | 37.42 | 30.91 | 29.18 |
| Chemical Formula (4) –200 nm | 63.91 @3.5 V | 59.69 | 64.81 @3 V | 35.61 | 30.45 | 28.51 |
| mCP –100 nm | 62.55 @3.5 V | 58.86 | 62.76 @3 V | 38.32 | 30.59 | 28.98 |

When o-4CbzBz is applied to the host materials mixed with FIrpic and mCP is applied to the second hole-transporting layer, the maximum current efficiency can be 62.55 cd/A and the maximum External Quantum Efficiency (EQE) can be 30.59%. On the other hand, when o-4CbzBz is applied to the second hole-transporting layer, the maximum current efficiency can be 64.09 cd/A, the maximum power efficiency can be 66.31 m/W and the maximum External Quantum Efficiency (EQE) can be 30.91%. Accordingly, o-4CbzBz applied to the hole transporting layer can increase the efficiency of the unit.

In summary, in the carbazole derivatives and the organic light-emitting diodes by using the same according to the present invention, it utilizes 1,3,5-Tris(carbazol-9-yl)benzene (TCP) or 1,2,4,5-tetra(9H-carbazol-9-yl)benzene (o-4Cbz) as a core structure and various kinds of electron-transporting groups as substituents at ortho-position to synthesize a series of bipolar host materials in phosphorescent organic light-emitting diodes with high luminous efficiency and good thermal stability. In addition, the carbazole derivatives of the present invention can also be applied to the hole transport layer. Moreover, 1,2,4,5-tetra(9H-carbazol-9-yl)benzene (o-4Cbz) can also be the host material and the hole transport layer material.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A carbazole derivative, comprising a structure of the following General Formula (1),

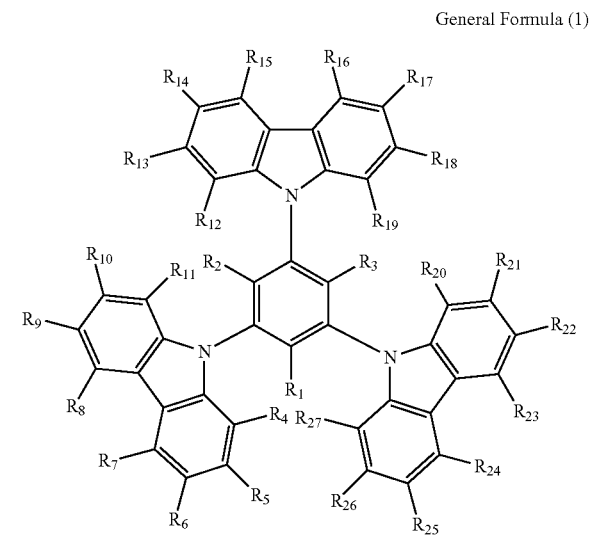

General Formula (1)

wherein $R_1$ is selected from the group consisting of the structures according to the following General Formula (2), General Formula (3) and General Formula (4),

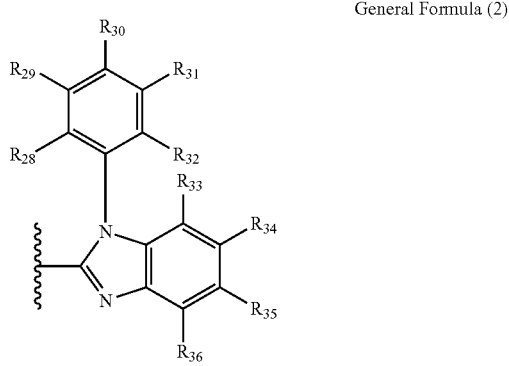

General Formula (2)

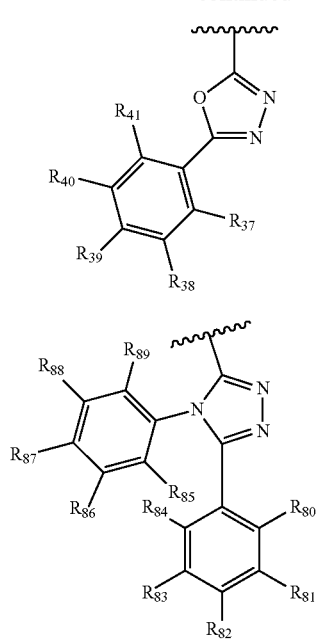

General Formula (3)

General Formula (4)

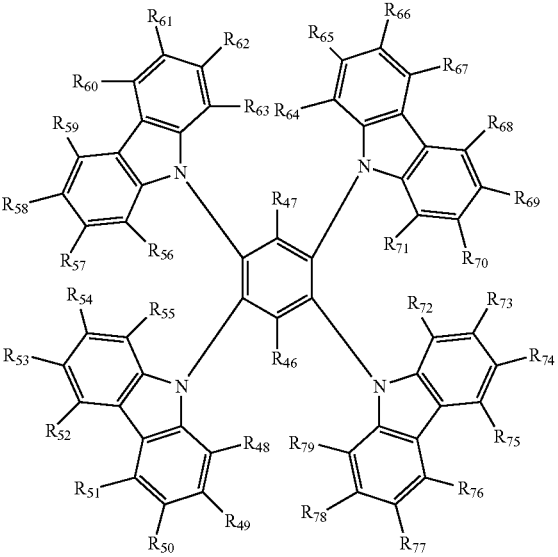

General Formula (5)

wherein $R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

2. The carbazole derivative of claim 1, wherein the alkyl group is selected from the group consisting of a substituted or unsubstituted straight-chain alkyl group with the carbon number of 1 to 6, and a substituted or unsubstituted branched-chain alkyl group with the carbon number of 3 to 6, the cycloalkyl group is a substituted or unsubstituted cycloalkyl group with the carbon number of 3 to 6, the alkoxy group is selected from the group consisting of a substituted or unsubstituted straight-chain alkoxy group with the carbon number of 1 to 6, and a substituted or unsubstituted branched-chain alkoxy group with the carbon number of 3 to 6, the haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6, the thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6, the silyl group is selected from the group consisting of a substituted or unsubstituted straight-chain silyl group with the carbon number of 1 to 6, and a substituted or unsubstituted branched-chain silyl group with the carbon number of 3 to 6, the alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

3. A carbazole derivative, comprising a structure of the following General Formula (5), wherein $R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group,

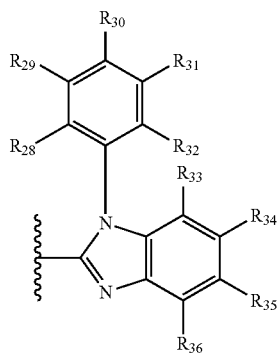

General Formula (2)

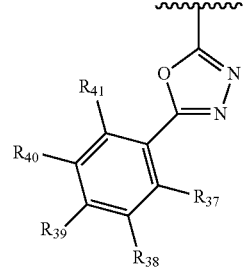

General Formula (3)

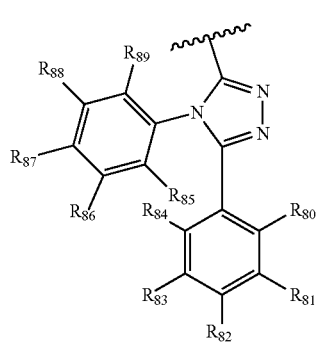

General Formula (4)

wherein $R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

4. The carbazole derivative of claim 3, wherein the alkyl group is selected from the group consisting of a substituted or unsubstituted straight-chain alkyl group with the carbon number of 1 to 6, and a substituted or unsubstituted branched-chain alkyl group with the carbon number of 3 to 6, the cycloalkyl group is a substituted or unsubstituted cycloalkyl group with the carbon number of 3 to 6, the alkoxy group is selected from the group consisting of a substituted or unsubstituted straight-chain alkoxy group with the carbon number of 1 to 6, and a substituted or unsubstituted branched-chain alkoxy group with the carbon number of 3 to 6, the haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6, the thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6, the silyl group is selected from the group consisting of a substituted or unsubstituted straight-chain silyl group with the carbon number of 1 to 6, and a substituted or unsubstituted branched-chain silyl group with the carbon number of 3 to 6, the alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

5. An organic light-emitting diode, comprising;
a first electrode layer;
a second electrode layer; and
an organic luminescent unit, disposed between the first electrode layer and the second electrode layer, wherein the organic luminescent unit has at least a carbazole derivative as shown in General Formula (1),

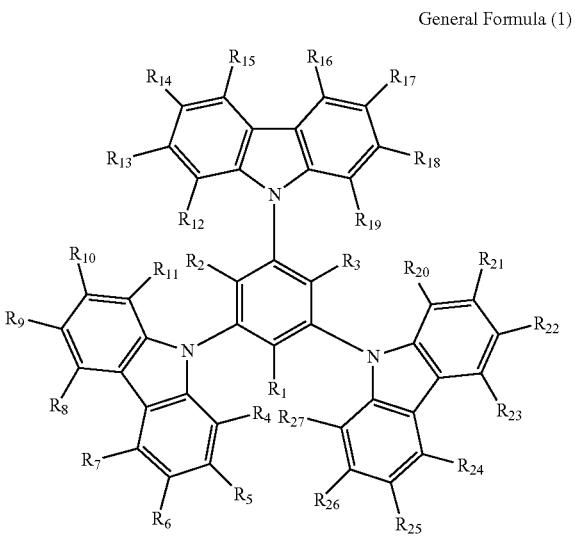

General Formula (1)

wherein $R_1$ is selected from the group consisting of the structures according to the following General Formula (2), General Formula (3) and General Formula (4),

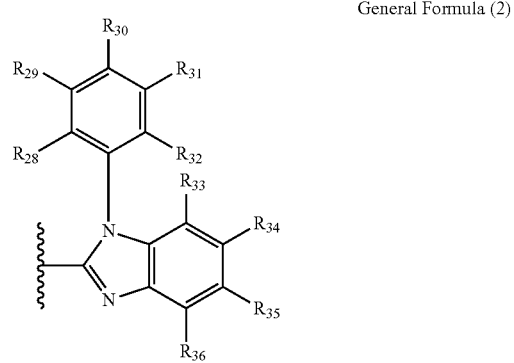

General Formula (2)

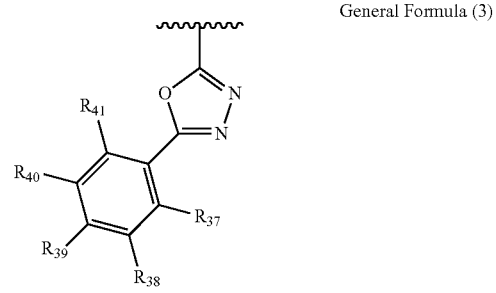

General Formula (3)

-continued

General Formula (4)

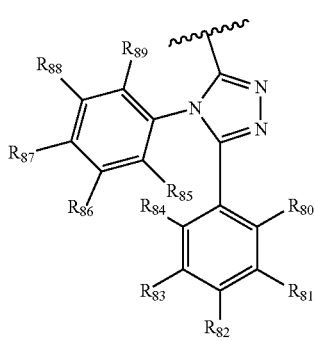

wherein $R_2$ to $R_{41}$ and $R_{80}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

6. The organic light-emitting diode of claim 5, wherein the alkyl group is selected from the group consisting of a substituted or unsubstituted straight-chain alkyl group with the carbon number of 1 to 6, and a substituted or unsubstituted branched-chain alkyl group with the carbon number of 3 to 6, the cycloalkyl group is a substituted or unsubstituted cycloalkyl group with the carbon number of 3 to 6, the alkoxy group is selected from the group consisting of a substituted or unsubstituted straight-chain alkoxy group with the carbon number of 1 to 6, and a substituted or unsubstituted branched-chain alkoxy group with the carbon number of 3 to 6, the haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6, the thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6, the silyl group is selected from the group consisting of a substituted or unsubstituted straight-chain silyl group with the carbon number of 1 to 6, and a substituted or unsubstituted branched-chain silyl group with the carbon number of 3 to 6, the alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

7. The organic light-emitting diode of claim 5, wherein the organic luminescent unit comprises an organic luminescent layer.

8. The organic light-emitting diode of claim 7, wherein the organic luminescent unit further comprises a hole transport layer and an electron transport layer, and the organic luminescent layer is disposed between the hole transport layer and the electron transport layer.

9. The organic light-emitting diode of claim 7, wherein the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

10. The organic light-emitting diode of claim 7, wherein the organic luminescent layer comprises a host material and a guest material, and the host material is the carbazole derivative and the guest material is a phosphorescent material.

11. The organic light-emitting diode of claim 10, wherein the content of the host material in the organic luminescent layer is between 60 vol % to 95 vol %.

12. The organic light-emitting diode of claim 10, wherein the content of the guest material in the organic luminescent layer is between 5 vol % to 40 vol %.

13. An organic light-emitting diode, comprising:
a first electrode layer;
a second electrode layer; and
an organic luminescent unit, disposed between the first electrode layer and the second electrode layer, wherein the organic luminescent unit has at least a carbazole derivative as shown in General Formula (5), General Formula (5)

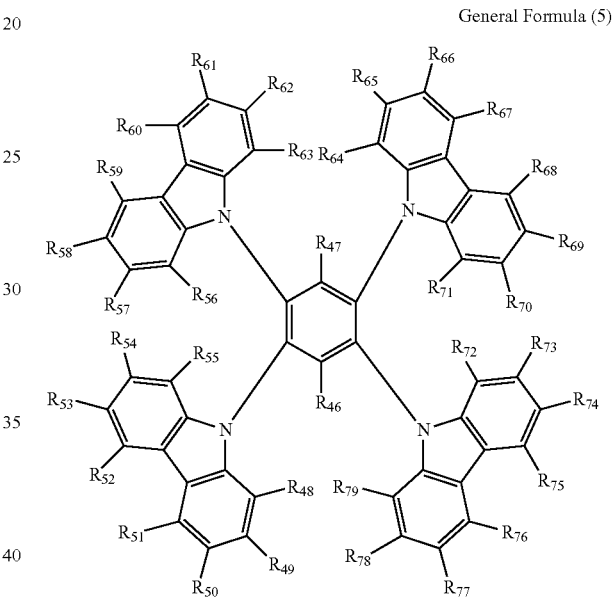

wherein $R_{46}$ is selected from the group consisting of the structures according to the following General Formula (2), General Formula (3) and General Formula (4), a hydrogen atom, a fluorine atom, a cyano group, an alkyl group, a cycloalkyl group, an alkoxy group, a haloalkyl group, a thioalkyl group, a silyl group and an alkenyl group, General Formula (2)

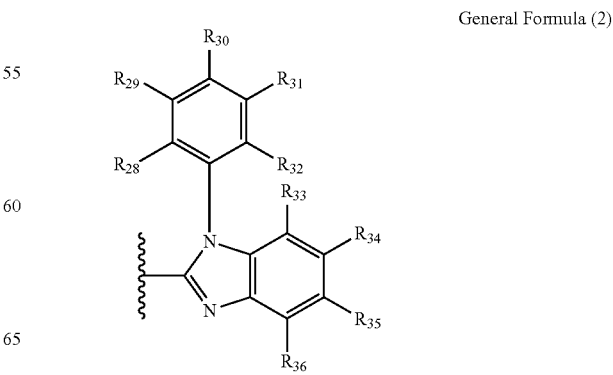

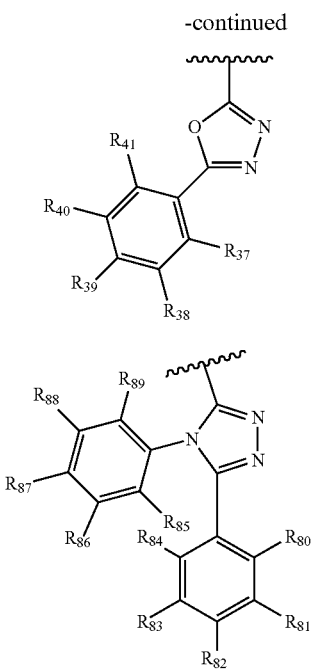

General Formula (3)

General Formula (4)

whererin $R_{28}$ to $R_{41}$ and $R_{47}$ to $R_{89}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

14. The organic light-emitting diode of claim 13, wherein the alkyl group is selected from the group consisting of a substituted or unsubstituted straight-chain alkyl group with the carbon number of 1 to 6, and a substituted or unsubstituted branched-chain alkyl group with the carbon number of 3 to 6, the cycloalkyl group is a substituted or unsubstituted cycloalkyl group with the carbon number of 3 to 6, the alkoxy group is selected from the group consisting of a substituted or unsubstituted straight-chain alkoxy group with the carbon number of 1 to 6, and a substituted or unsubstituted branched-chain alkoxy group with the carbon number of 3 to 6, the haloalkyl group is selected from the group consisting of a substituted or unsubstituted straight-chain haloalkyl group with the carbon number of 1 to 6, and a substituted or unsubstituted branched-chain haloalkyl group with the carbon number of 3 to 6, the thioalkyl group is selected from the group consisting of a substituted or unsubstituted straight-chain thioalkyl group with the carbon number of 1 to 6, and a substituted or unsubstituted branched-chain thioalkyl group with the carbon number of 3 to 6, the silyl group is selected from the group consisting of a substituted or unsubstituted straight-chain silyl group with the carbon number of 1 to 6, and a substituted or unsubstituted branched-chain silyl group with the carbon number of 3 to 6, the alkenyl group is selected from the group consisting of a substituted or unsubstituted straight-chain alkenyl group with the carbon number of 2 to 6, and a substituted or unsubstituted branched-chain alkenyl group with the carbon number of 3 to 6.

15. The organic light-emitting diode of claim 13, wherein the organic luminescent unit comprises an organic luminescent layer.

16. The organic light-emitting diode of claim 15, wherein the organic luminescent unit further comprises a hole transport layer and an electron transport layer, and the organic luminescent layer is disposed between the hole transport layer and the electron transport layer.

17. The organic light-emitting diode of claim 15, wherein the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

18. The organic light-emitting diode of claim 15, wherein the organic luminescent layer comprises a host material and a guest material, and the host material is the carbazole derivative and the guest material is a phosphorescent material.

19. The organic light-emitting diode of claim 18, wherein the content of the host material in the organic luminescent layer is between 60 vol % to 95 vol %.

20. The organic light-emitting diode of claim 18, wherein the content of the guest material in the organic luminescent layer is between 5 vol % to 40 vol %.

* * * * *